(12) United States Patent
Herchen et al.

(10) Patent No.: US 8,802,331 B2
(45) Date of Patent: Aug. 12, 2014

(54) NON-DESTRUCTIVE TESTING METHODS FOR FUEL CELL INTERCONNECT MANUFACTURING

(75) Inventors: Harald Herchen, Los Altos, CA (US); Martin Janousek, Sunnyvale, CA (US)

(73) Assignee: Bloom Energy Corporation, Sunnyvale, CA (US)

( * ) Notice: Subject to any disclaimer, the term of this patent is extended or adjusted under 35 U.S.C. 154(b) by 10 days.

(21) Appl. No.: 13/306,511

(22) Filed: Nov. 29, 2011

(65) Prior Publication Data

US 2012/0135337 A1    May 31, 2012

Related U.S. Application Data

(60) Provisional application No. 61/418,043, filed on Nov. 30, 2010.

(51) Int. Cl.
*H01M 8/02* (2006.01)
*H01M 8/04* (2006.01)
*G01N 27/72* (2006.01)
*G01N 27/82* (2006.01)
*G01N 21/95* (2006.01)
*G01N 29/24* (2006.01)
*G01N 29/07* (2006.01)

(52) U.S. Cl.
CPC ............ *G01N 29/2418* (2013.01); *G01N 21/95* (2013.01); *H01M 8/0202* (2013.01); *G01N 27/82* (2013.01); *G01N 29/07* (2013.01)
USPC ........... 429/535; 429/400; 429/517; 429/522; 324/200

(58) Field of Classification Search
CPC ..... H01M 8/02–8/0245; H01M 8/04–8/04074; H01M 8/04291–8/04686; H01M 8/04962–8/04985
USPC ............................ 429/10, 428–450, 517–535
See application file for complete search history.

(56) References Cited

U.S. PATENT DOCUMENTS

| 2,176,784 | A  | * | 10/1939 | Bowden | 209/215 |
| 5,589,772 | A  | * | 12/1996 | Kugai | 324/240 |
| 6,426,161 | B1 | * | 7/2002 | Cisar et al. | 429/514 |
| 6,599,651 | B1 | * | 7/2003 | Saitou et al. | 429/509 |

(Continued)

FOREIGN PATENT DOCUMENTS

| JP | 2000-285934 A | 10/2000 |
| JP | 2007-042406 A | 2/2007 |

OTHER PUBLICATIONS

Fialkov, A., Davidovich, Y., Pshenichkin, P., Galeev, G., (Aug. 1965). Diamagnetic Susceptibility and Linear Thermal Expansion of Graphitized Carbons. Soviet Powder Metallurgy and Metal Ceramics. vol. 4, Issue 8, pp. 674-680.*

(Continued)

*Primary Examiner* — Jonathan Crepeau
*Assistant Examiner* — Jacob Buchanan
(74) *Attorney, Agent, or Firm* — The Marbury Law Group PLLC

(57) ABSTRACT

Various embodiments provide methods for testing a fuel cell interconnect including the steps of providing a fuel cell interconnect and performing a non-destructive test on the fuel cell interconnect comprising at least one of detecting a magnetic response of the interconnect, calculating a volume by optically illuminating the interconnect, detecting an acoustic response of the interconnect, and detecting a thermal response of the interconnect.

21 Claims, 22 Drawing Sheets

(56) References Cited

U.S. PATENT DOCUMENTS

2004/0095127 A1* 5/2004 Mohri et al. .............. 324/117 R
2005/0142431 A1   6/2005 Shimomura et al.
2006/0127711 A1* 6/2006 Kaschmitter et al. ........... 429/13
2008/0199738 A1* 8/2008 Perry et al. ..................... 429/12

OTHER PUBLICATIONS

International Search Report & Written Opinion issued in PCT Application No. PCT/US2011/062328, mailed on Aug. 1, 2012.

* cited by examiner

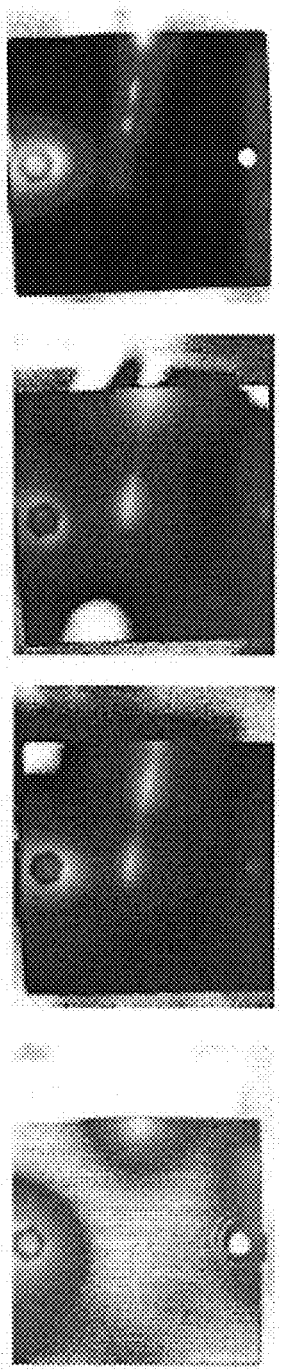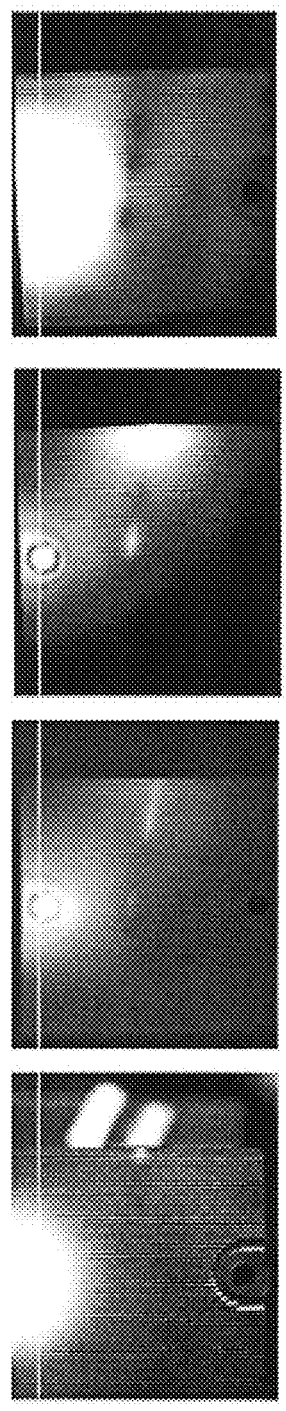
FIG. 17A
FIG. 17B

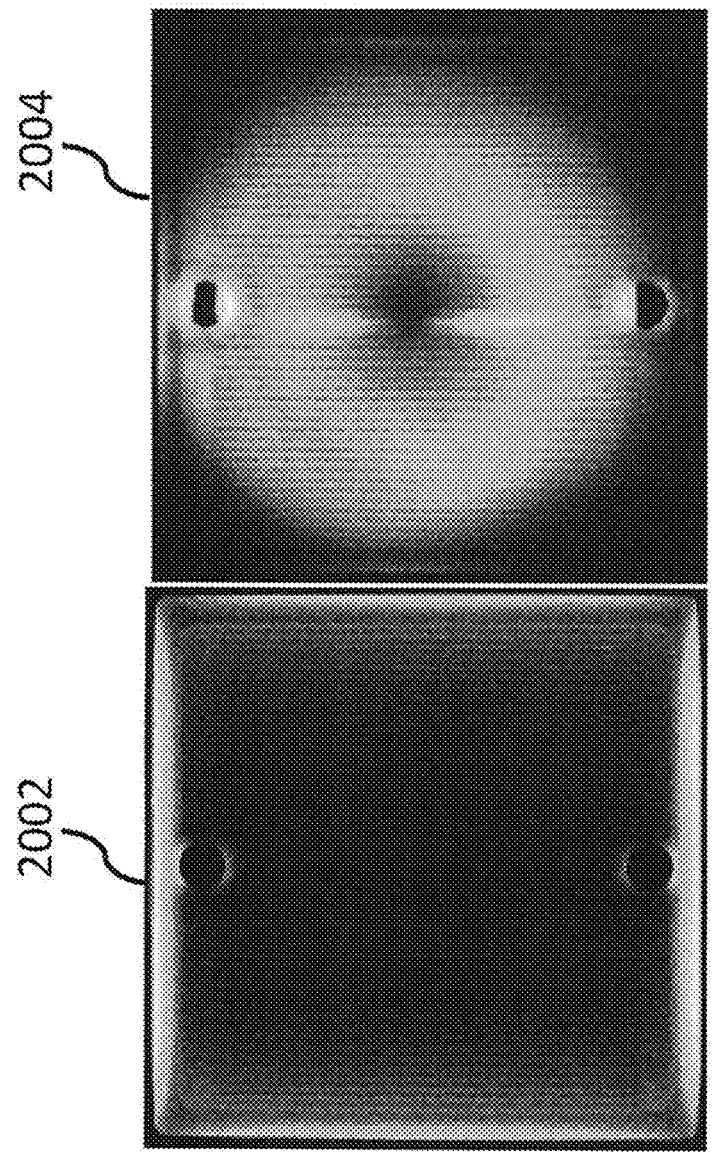

NON-DESTRUCTIVE TESTING METHODS FOR FUEL CELL INTERCONNECT MANUFACTURING

CROSS-REFERENCE TO RELATED APPLICATIONS

This application claims the benefit of priority to U.S. Provisional Patent Application Ser. No. 61/418,043 filed Nov. 30, 2010, which is hereby incorporated herein by reference in its entirety.

BACKGROUND

In a high temperature fuel cell system, such as a solid oxide fuel cell (SOFC) system, an oxidizing flow is passed through the cathode side of the fuel cell while a fuel flow is passed through the anode side of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit.

In order to optimize the operation of SOFCs, the oxidizing and fuel flows should be precisely regulated. Therefore, the flow regulating structures, such as interconnects in the fuel cell system should be precisely manufactured.

SUMMARY

Various embodiments provide non-destructive methods for testing a fuel cell interconnect including steps of providing a fuel cell interconnect and performing a non-destructive test on the fuel cell interconnect comprising at least one of detecting a magnetic response of the interconnect, calculating a volume by optically illuminating the interconnect, detecting an acoustic response of the interconnect, and detecting a thermal response of the interconnect.

Further embodiments include methods for testing a fuel cell interconnect including the steps of providing a fuel cell interconnect and detecting a magnetic response of the interconnect as a function of position across the interconnect.

Further embodiments include methods for testing an interconnect including the steps of providing a interconnect having multiple faces, placing the interconnect in a striped white light illumination field, and calculating a height of each of the multiple faces of the interconnect as a function of length and width based on locations of reflected light stripes. The sample may be rotated to expose each different face to the striped light for the calculations. This embodiment may also include the steps of using the calculated heights and the angles of rotation to model the interconnect in three dimensional space and calculating the enclosed volume of the model.

Further embodiments include methods for testing a fuel cell interconnect including steps for providing a fuel cell interconnect, applying an acoustic excitation to the fuel cell interconnect, detecting an acoustic response, and determining at least one of a interconnect density, a interconnect coefficient of thermal expansion, and a speed of sound in the interconnect based on the acoustic response.

Further embodiments include methods for testing interconnects including steps for providing the interconnect, stimulating the interconnect, and detecting a thermal response of the interconnect.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIGS. 17A and 17B are a series of infrared images showing infrared phase and amplitude, respectively, resulting from sweeping the ultrasonic excitation.

FIGS. 20A and 20B are schematic top views of infrared images of non-defective and defective interconnects, respectively.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments provide systems and methods for testing material properties. These methods may be non-destructive, such that the interconnect is not damaged or destroyed during testing and may be later used in a fuel cell. Further embodiments employ these systems and methods in the improved manufacture and selection of components for fuel cell systems. Fuel cell components manufactured precisely, such as those with uniform density and coefficient of thermal expansion, may improve fuel cell system efficiency.

Figure 1:
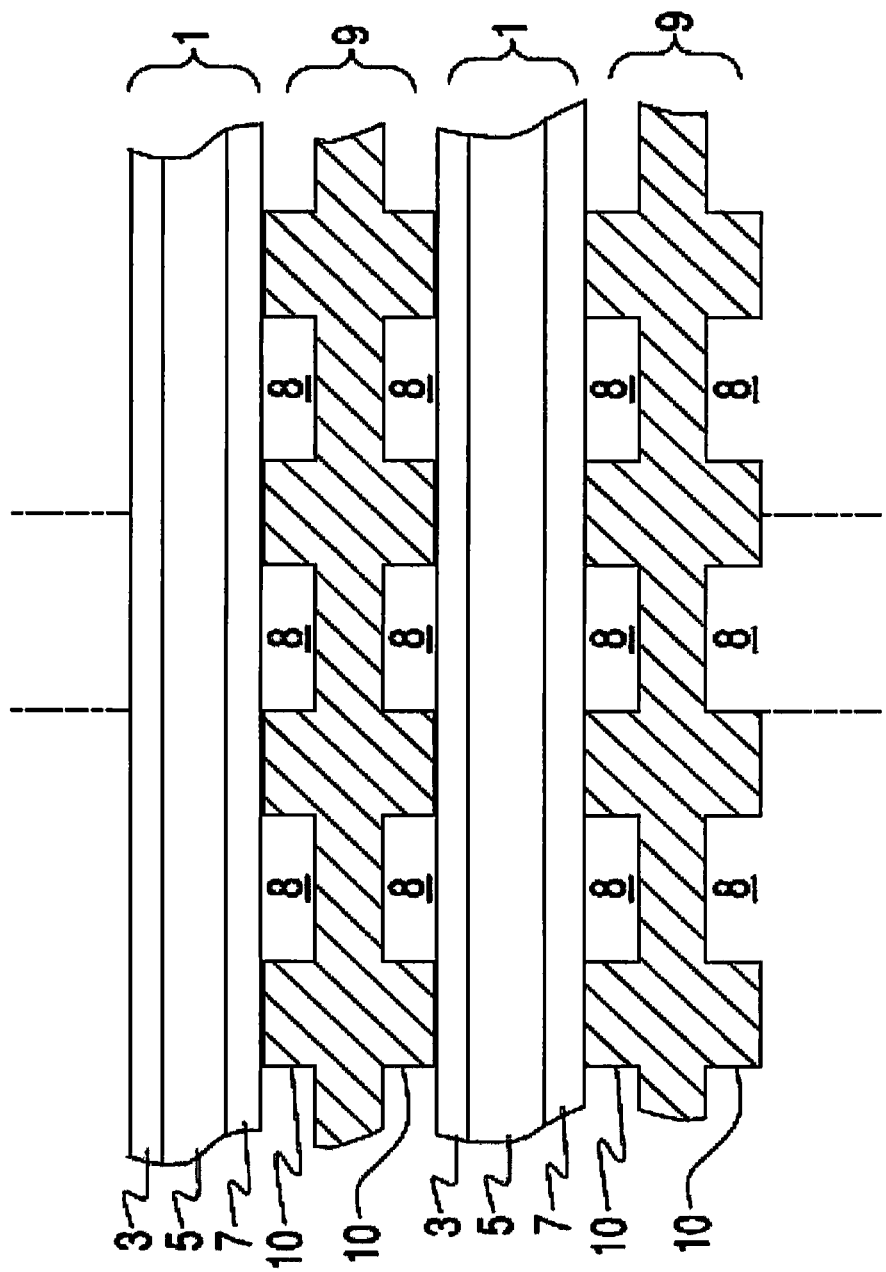
FIG. 1 illustrates a side cross-sectional view of a SOFC stack.

FIG. 1 illustrates a SOFC stack in which each SOFC 1 comprises a cathode electrode 7 (e.g., LSM or other conductive perovskites), a solid oxide electrolyte 5 (e.g., YSZ, ScSZ, or doped ceria), and an anode electrode 3 (e.g., a cermet such as a nickel-stabilized zirconia and/or doped ceria cermet). Fuel cell stacks are frequently built from a multiplicity of SOFC's 1 in the form of planar elements, tubes, or other geometries. Fuel and air has to be provided to the electrochemically active surface, which can be large.

The gas flow separator 9 (referred to as a gas flow separator plate when part of a planar stack), containing gas flow passages or channels 8 between ribs 10, separates the individual cells in the stack. The gas flow separator plate separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. At either end of the stack, there may be an air end plate or fuel end plate (not shown) for providing air or fuel, respectively, to the end electrode.

Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. FIG. 1 shows that the lower SOFC 1 is located between two interconnects 9. Interconnects may be made of a chromium alloy, such as a chromium alloy with 4-6% iron by weight.

The various fuel cell components must be precisely manufactured to maximize fuel cell efficiency. Specifically, components with densities and coefficients of thermal expansion which are both uniform and have an average value within a predetermined range are desired. The embodiment methods and systems provide ways to help manufacture interconnects with these properties.

A first set of embodiments rely on magnetism to indicate the distribution of the coefficient of thermal expansion. A fixed magnet and load cell may be used to measure the attractive force of an interconnect to the magnet as a function of position across the interconnect. The natural logarithm of the attractive force has been found to be linearly correlated with the coefficient of thermal expansion (CTE) in metal alloy parts, such as solid oxide fuel cell interconnects. Preferably, the metal parts, such as interconnects, comprise a chromium based alloy, such as 4-6 wt % Fe and 94-96 wt % Cr. The alloy may optionally contain one or more of Y, Co and Cu (e.g., 0 to 1 wt % of Y, Co and/or Cu). Therefore a room temperature indication of the CTE (e.g., average CTE value) can be obtained by measuring the magnetic attraction between the metal part and the magnet. The mapping allows the non-uniformity of such attraction to determined, which allows the determination of the uniformity of the CTE.

Figure 2:
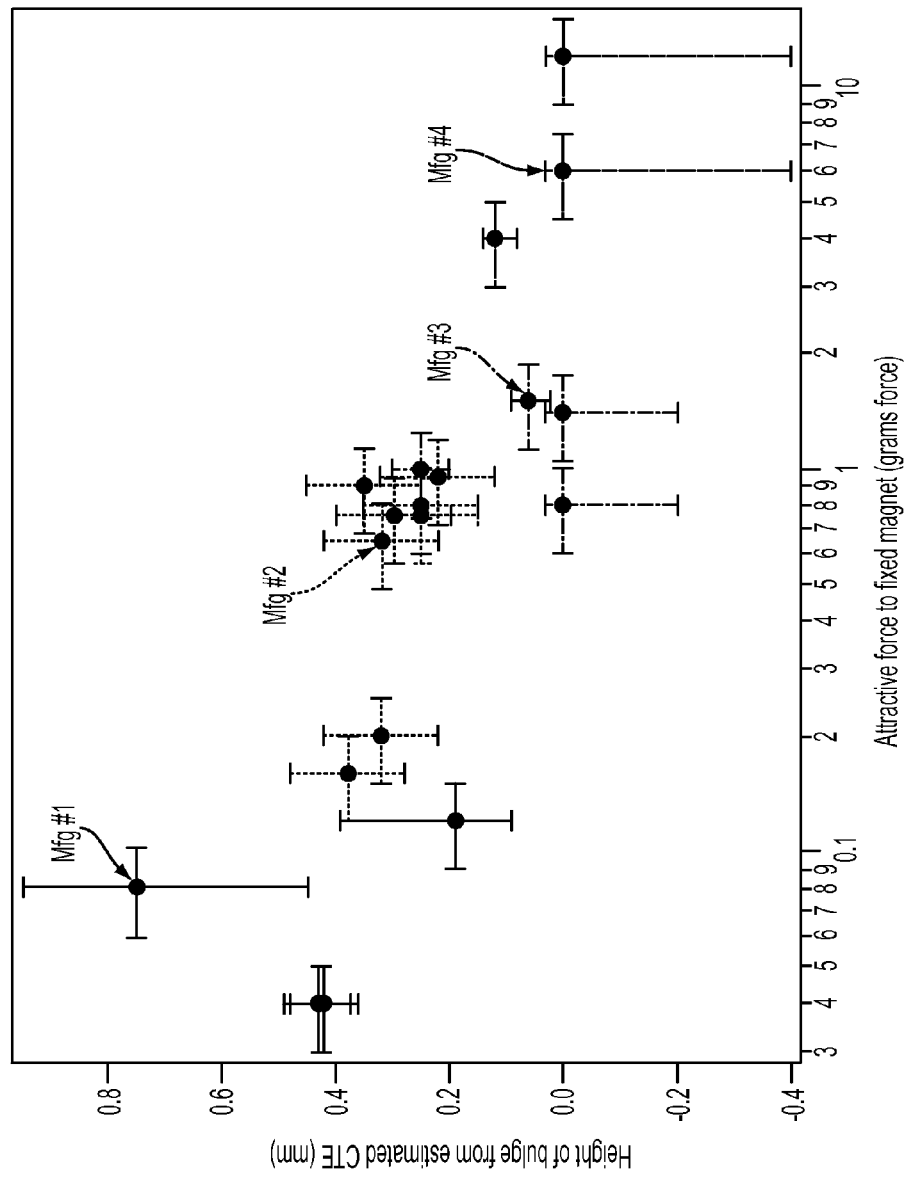
FIG. 2 is a plot illustrating the inverse correlation of magnetic response and coefficient of thermal expansion.

An additional benefit for manufacturing is that by placing the magnetic probe near an uncoated interconnect surface, the manufacturers or source of the interconnects can be distinguished by the varying amount of attraction their interconnects exhibit. For example, FIG. 2 illustrates a variation in magnetic response from interconnects made to the same specification by four different manufacturers (labeled Mfg#1 to Mfg#4). Specifically, FIG. 2 illustrates the "height of the bulge" in millimeters from the estimated CTE as a function of the log plot of attractive force of the interconnect to a fixed magnet in units of grams force for interconnects from the four different manufacturers.

Without wishing to be bound by any particular theory of operation, the present inventors believe that superparamagnetism associated with small ferro- or ferri-magnetic particles may be correlated with the CTE. Specifically, the iron (Fe) in the chromium (Cr) based interconnect is introduced primarily to adjust the CTE to match that of the electrolyte in the SOFC stack. The Fe is introduced as a powder into powdered Cr, and the Fe diffuses into the Cr at the high sintering temperatures the part is exposed to during manufacture. The amount of diffusion varies depending on particle surface oxidation states or other barriers to diffusion. Since Fe is soft, if it is not fully diffused in, then the CTE will be lower, or more closely matching that of pure Cr.

The magnetic susceptibility varies by several orders of magnitude depending on the process, so the load cell needs to have good linearity, and the magnetic flux needs to be spatially uniform or controlled over the thickness of the interconnect.

A room temperature indication of thermal expansion offers a significant advantage in terms of manufacturing for two reasons. One is that the parts can be tested without heating (e.g., at 50° C. or below, such as 20 to 50° C. including room temperature) and without sensitive thermal expansion measurements. The other is that the CTE can be mapped out over the part in a non-destructive fashion. That aids in ensuring the CTE is uniform, which is key for high yields in SOFC manufacture.

It may be possible to obtain better measurements with smaller probes, as well as probes that account for the rib structure 10 on the interconnects used for fluid flow. In addition, the CTE differences that matter are on the order of 0.1%, while the magnetic susceptibility varies by orders of magnitude, so it is much more sensitive.

In an example embodiment method, a smaller diameter magnet (~3.5 mm) was placed on a scale with milligram resolution. A platform was placed over the scale, with a hole for the magnet. The interconnect under test was placed on the platform, the bottom of which was 3 mm above the top of the magnet. The interconnect was manually scanned across the hole, and a camera recorded the location of the interconnect, and the weight reading of the magnet, obviously as influenced by the local attraction to the interconnect. The gap of 3 mm is large enough to keep the variation in gap due to interconnect curvature to a few percent of the reading. The setup was meant to get some initial data, not provide the best possible values. Edge effects and delay in response may introduce some error in the reading.

Figure 3:
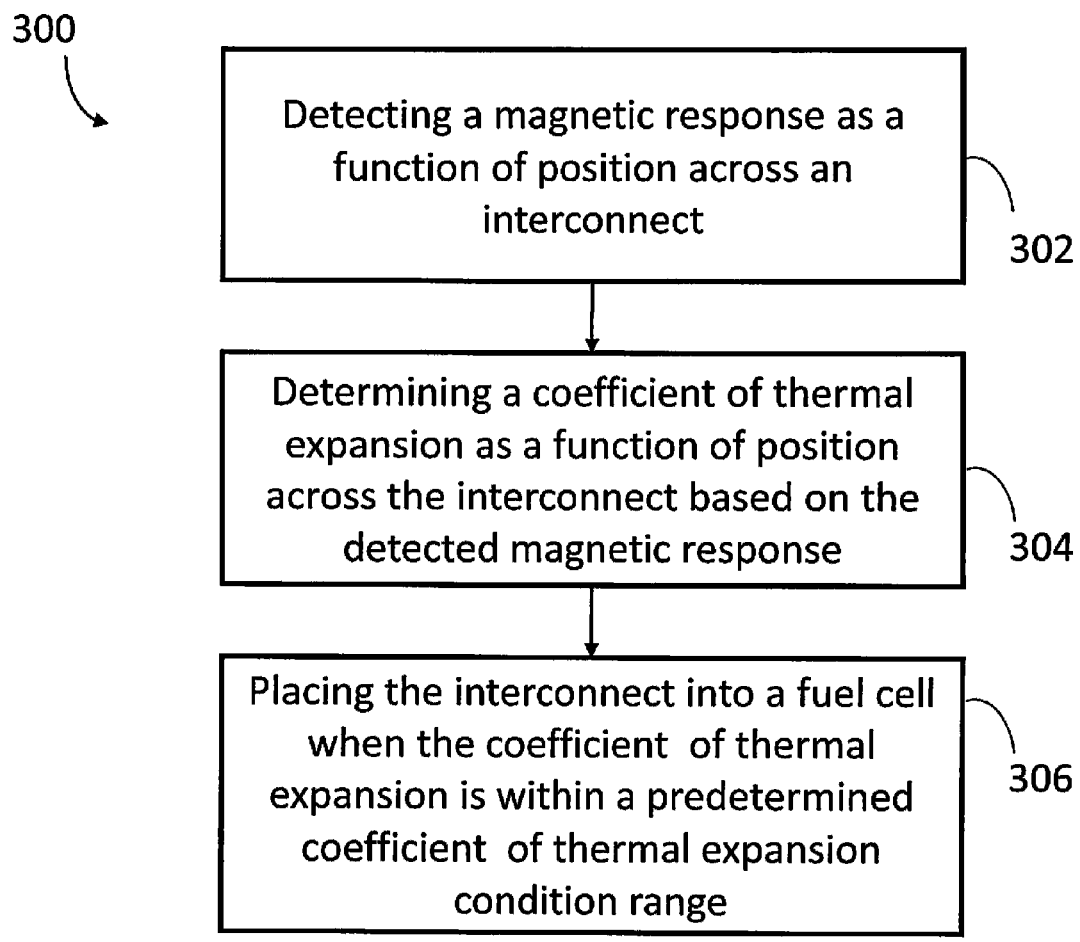
FIG. 3 is a flow chart illustrating an embodiment method for testing an interconnect with magnetic response.

FIG. 3 illustrates an embodiment method 300. In step 302, a magnetic response, such as magnetic susceptibility or another suitable magnetic response, may be detected across an interconnect. Magnetic response may be determined as in the example above by measuring a weight reading of a magnet influenced by the attraction of the interconnect. Magnetic response across the interconnect may be measured in other ways, such as by using one of a variety of different magnetometers. In step 304, the coefficient of thermal expansion as a function of position across the interconnect may be determined based on the measured magnetic response. For example, the coefficient of thermal expansion may be determined based on its inverse correlation with the magnetic response, such as susceptibility.

In step 306, the interconnect is placed in a fuel cell stack if the average determined coefficient of thermal expansion across the interconnect is within a predetermined range (e.g., within 5%, such as within 1% average CTE of solid oxide fuel cells to be used in a stack with the interconnects) and/or if the CTE is within an acceptable level of uniformity across the interconnect (e.g., if the CTE uniformity varies by less than 10%, such as less than 1%, across the interconnect). This step may allow manufacturers to avoid using non-CTE matched and/or non-uniform interconnects. If the average value of CTE is too far removed from the fuel cell CTE and/or if range of the coefficient of thermal expansion measured across the interconnect is too large such that it would interfere with fuel cell stack efficiency, the interconnect is not placed in the fuel cell.

If desired, step 304 may be omitted. In this case, the measured value of the magnetic response, such as susceptibility, in step 302 is correlated or compared to a database (e.g., a look up table) of acceptable and non-acceptable values of magnetic response by a person or a machine, such as a computer, and the decision in step 306 is made based on the correlation or comparison.

Further embodiment methods test the volume and density of the compacted metal powder parts used to manufacture interconnects. In this embodiment, the volume is calculated by optical illumination of the part, with the resulting data from various angles being combined electronically to determine the volume.

Figure 4:
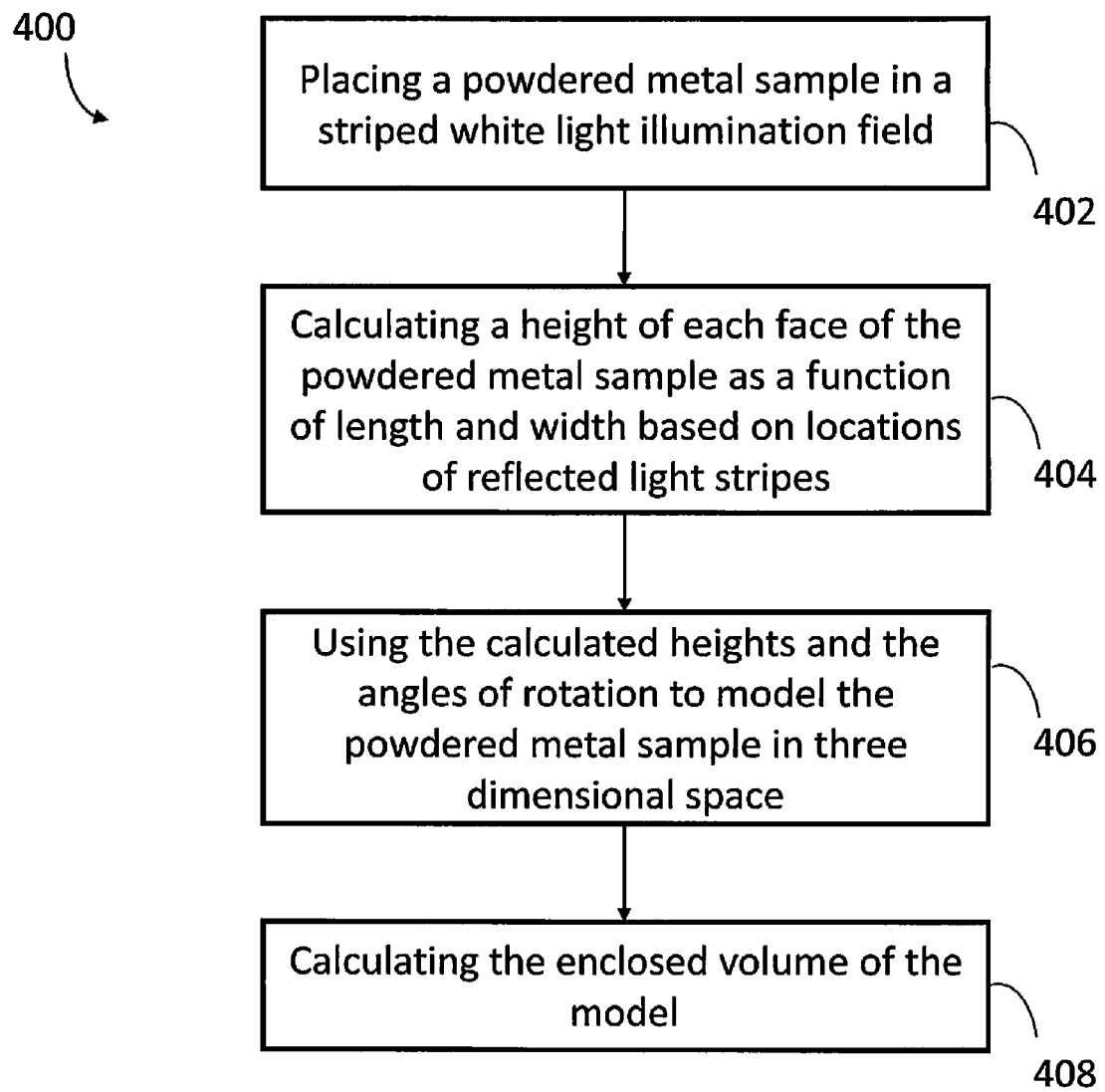
FIG. 4 is a flow chart illustrating an embodiment method for testing the volume of a compacted metal powder sample.

An example embodiment method 400 of determining volume is illustrated in FIG. 4. A compacted metal powder sample may either be an unsintered, compacted metal powder part or a compacted, sintered metal part that is generated later in the powder metallurgy process. A typical sample may be one to three mm long on each side. Although the method is described with respect to compacted metal powder samples, the method may also be applied to interconnects in further embodiments.

In step 402, a sample may be placed in a striped white light illumination field such that the location of the stripes at an angle away from the illumination may be observed. In step 404, the reflected stripes may be used to calculate the z-height information of the sample as a function of x and y. The sample may be rotated approximately 90 degrees to illuminate another face to obtain the z heights for that orientation. This may be repeated until all faces have been observed, which may involve four to six measurements typically. Software may be used to combine the full set of observed z heights to make a 3D model of the sample, step 406. A general or special purpose computer or any suitable processor or logic may calculate the enclosed volume of the model, step 408.

The density of the compacted metal powder sample may also be determined. The weight of the sample may be measured. For example, the sample may be weighed with a relatively high resolution scale, such as with approximately five significant figures. Density may be calculated by dividing the weight by the volume determined by the embodiments methods described above. In some embodiments, the weight may be measured before and after the volume determination to make sure that nothing changed.

This method avoids the problems other methods face such as bubbles, fluid penetration into the part, and influence of wires holding the sample in the liquid. The result is that the accuracy is improved by a factor of ten or more, allowing small variations in density which affect connected porosity to be detected more easily.

Figure 5A:
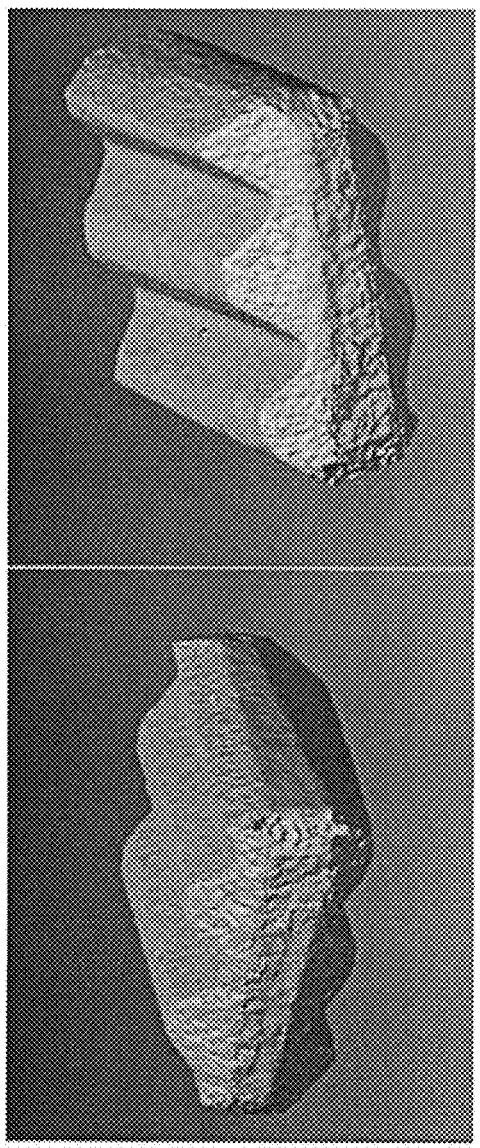
FIGS. 5A and 5B are computer generated images of a 3D model of a compacted powder metal sample.

Some related test data are shown in FIG. 5A. A small sample of compacted metal powder was prepared, and the method applied. The volume of the resulting solid model is calculated from the model to be 42.743 $mm^3$.

Figure 5B:
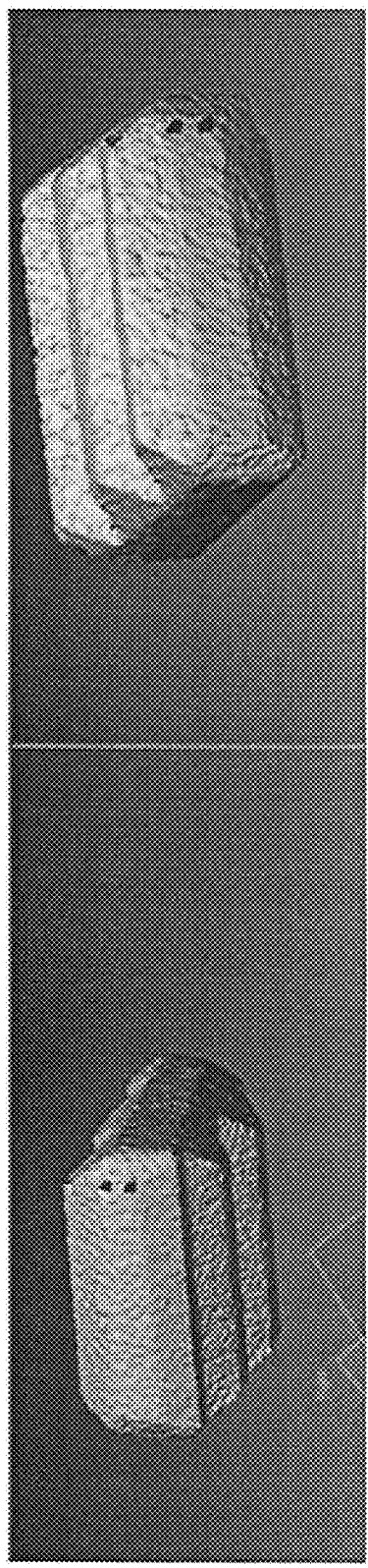

Additional test data are shown in FIG. 5B. Two small samples of compacted metal powder were prepared, and the optical method applied. The weights of each part were also measured, and combined with the volumes give densities of 6.718 and 6.660 $g/cm^3$.

Error sources are largely due to two sources: z height resolution of the sensor, and errors in combining the images due to distortion of the maps. The z height resolution for these small samples is in the 1 to 2 micron range and the distortion with good lenses is a fraction of a percent.

With this level of resolution, the density is expected to be calculated to the fourth significant figure (third decimal place) with good assurance. The method described above with respect to FIGS. 4, 5A and 5B may be non-destructive or destructive. For example, if the sample includes an entire sintered interconnect, then the method is non-destructive. However, if the sample includes a piece cut from the sintered interconnect, as shown in FIGS. 5A and 5B, then the method is destructive. An entire interconnect is easier to measure, but cut pieces from an interconnect allows the measurement to take into account local density variations.

Further embodiments may include non-destructive methods for testing fuel cell parts with acoustic excitation. The present inventors realized that the coefficient of thermal expansion, speed of sound, and resonant frequencies of a part are all related to interatomic potential of the part material and therefore to each other. Various embodiment methods and systems provide ways to help manufacture and sort components with the desired coefficient of thermal expansion based on these related properties.

These embodiments may involve applying an acoustic excitation (e.g., one or more pings or signals) to the part, detecting an acoustic response, and determining one or more properties of the part based on the acoustic response.

Figure 6:
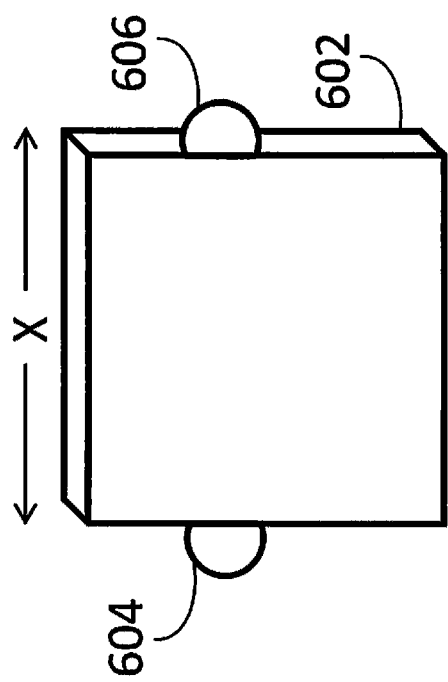
FIG. 6 illustrates a fuel cell interconnect with transducers for generating and receiving a ping.

Various embodiments may rely on one or more pings (e.g., one or more sound and/or ultrasound pulses) to determine properties of fuel cell components. FIG. 6 illustrates an example setup for providing a ping to a fuel cell component 602, such as an interconnect 9, electrolyte 5, or end plate of a stack. An end plate is similar to an interconnect except that an end plate is located at the end of the stack adjacent to only one fuel cell, while an interconnect is located between two fuel cells. A first transducer 604 may be attached to the component 602. A second transducer 606 may be attached to the opposite side of the component 602 a distance X from the first transducer 604 as shown in FIG. 6. Each transducer may be configured to provide a ping, detect a ping, or both.

Figure 7A:
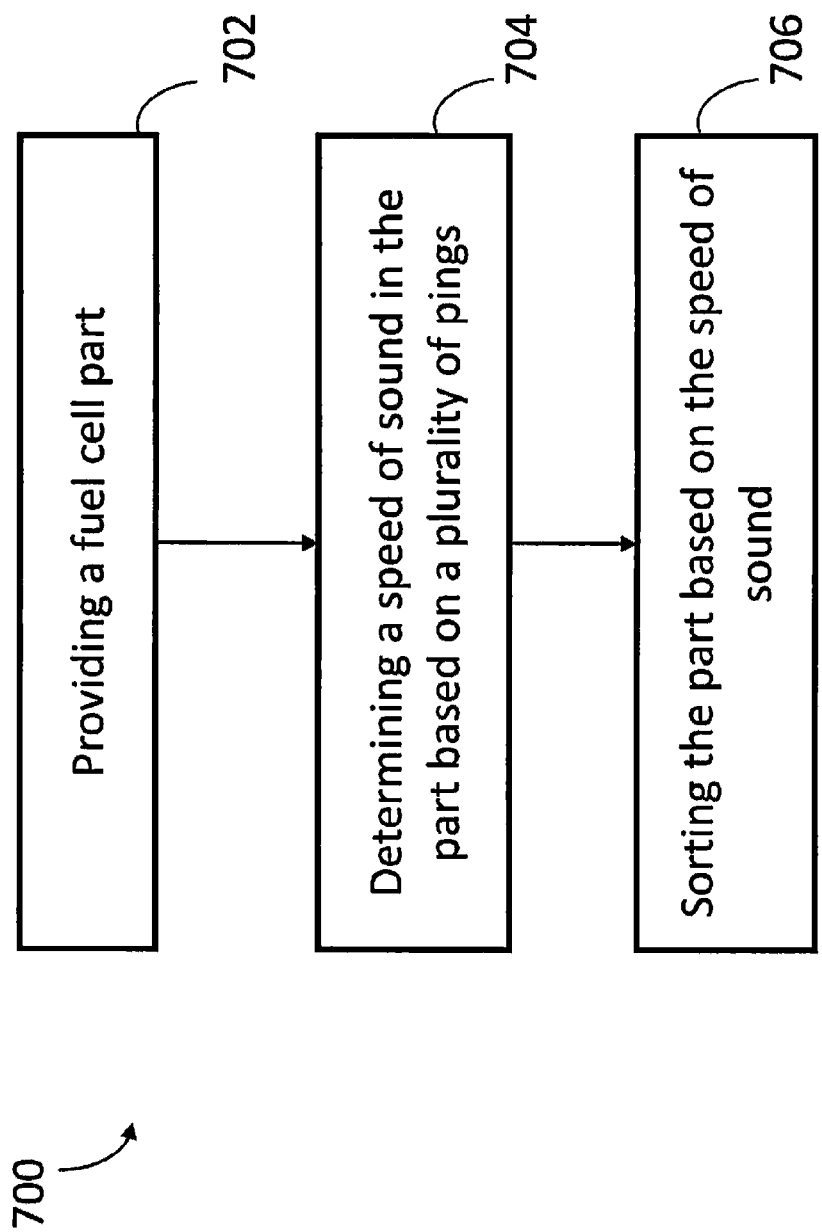
FIG. 7A is a process flow chart illustrating an embodiment method for testing a fuel cell interconnect based on the speed of sound.

FIG. 7A illustrates an embodiment method 700. A fuel cell part, such as any of the components discussed above, may be provided in step 702. In step 704, a speed of sound may be determined in the part based on one or more pings. A ping may be a short pulse of acoustic energy generated by a transducer. In various embodiments, the ping may be an ultrasound signal. Measurements of a ping may be made by any suitable ultrasound detector or analyzer based on output from transducers 704, 706. The part may be sorted based on the speed of sound in step 706. Sorting may include selecting or deselecting the component to be included in a fuel cell stack. Various types of sorting may be used, such as using a lookup table to determine if the measured speed of sound falls within one or more predetermined ranges. In further embodiments, the speed of sound may be correlated to a coefficient of thermal expansion, such as based on data from previously measured parts, and the part may be sorted based on the correlated coefficient of thermal expansion. Sorting may be done manually based on the output of an ultrasound detector or by a machine such as a robotic arm directed by a controller based on measurements in step 704.

Figure 7B:
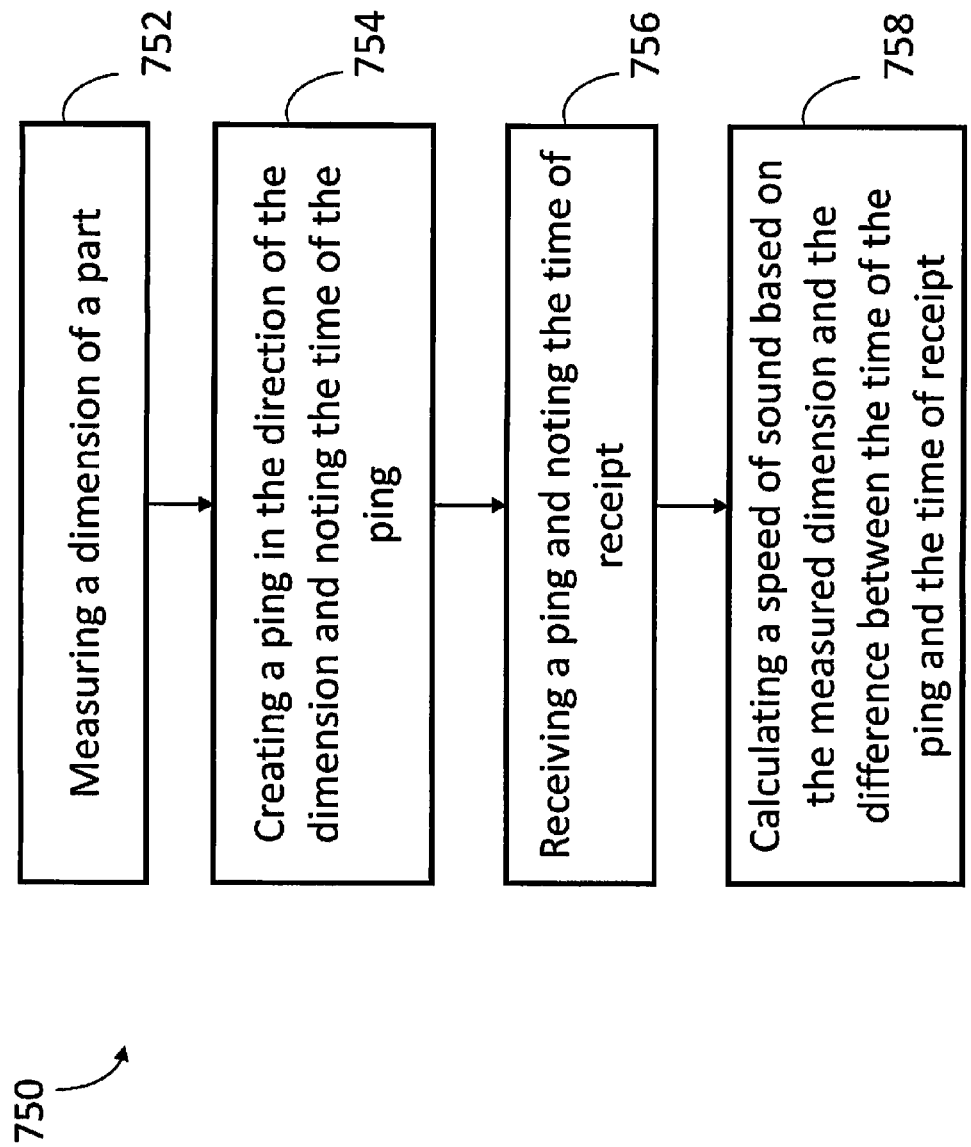
FIG. 7B is a process flow chart illustrating an embodiment method for measuring the speed of sound with a ping.

Various embodiments may include different methods for measuring the speed of sound in step 704. FIG. 7B illustrates an example method 750 for finding the speed of sound for a fuel cell part. A dimension of the part may be measured in step 752. For example, the dimension X (e.g. length) between the first and second transducer may be measured (e.g., manually or by machine, such as by a laser length measurement system). A ping may be created in step 754. The ping may be a short pulse of acoustic energy generated by a first transducer 604. The time of the ping may be noted (e.g. by an ultrasound detector or analyzer). In step 756, the ping may be detected or received at the second transducer 606 (e.g. by the ultrasound detector or analyzer). The time of arrival may be noted. In step 758, a speed of sound for the part may be calculated based on the measured dimension and the difference between the time of the ping creation and the time of ping receipt. For example, the dimension X may be divided by the difference between the time of the ping creation and the time of ping receipt to determine the speed of sound.

Further embodiments may involve multiple pings. For example, various embodiments may involve transducers ping back and forth. A first transducer 604 may generate ping which is detected at a second transducer 606. As soon as the first ping is detected, the second transducer 606 may respond by generating another ping which is received at the first transducer 604. A time of generation and receipt could be noted for each ping, and a speed of sound calculated based on the dimension X and the time differences for each ping. These speeds could be averaged. Pings may continue as many times as desired to increase signal to noise ratio.

Further embodiments may involve pings in different locations on the fuel cell part. For example, multiple pings may be generated and received as described above. These multiple pings may again be used to calculate multiple speeds of sound, which in turn may be averaged. However, the transducers 604 and 606 may be moved between one or more pings. For example, the transducers 604, 606 may be moved up and down the sides of the part 602. A new dimension X may be measured between the transducers 604 and 606 (if the distance X between the transducers changed after the movement) for each ping and used to calculate the corresponding speed of sound. Further, the locations of the transducers 604 and 606 may be noted such that the speed of sound may be mapped across the part. Speed of sound may be correlated with a coefficient of thermal expansion, and therefore, the coefficient of thermal expansion may also be mapped across the part. Such mapping may be used to ensure that the part and the coefficient of thermal expansion across the part are uniform.

Figure 8:
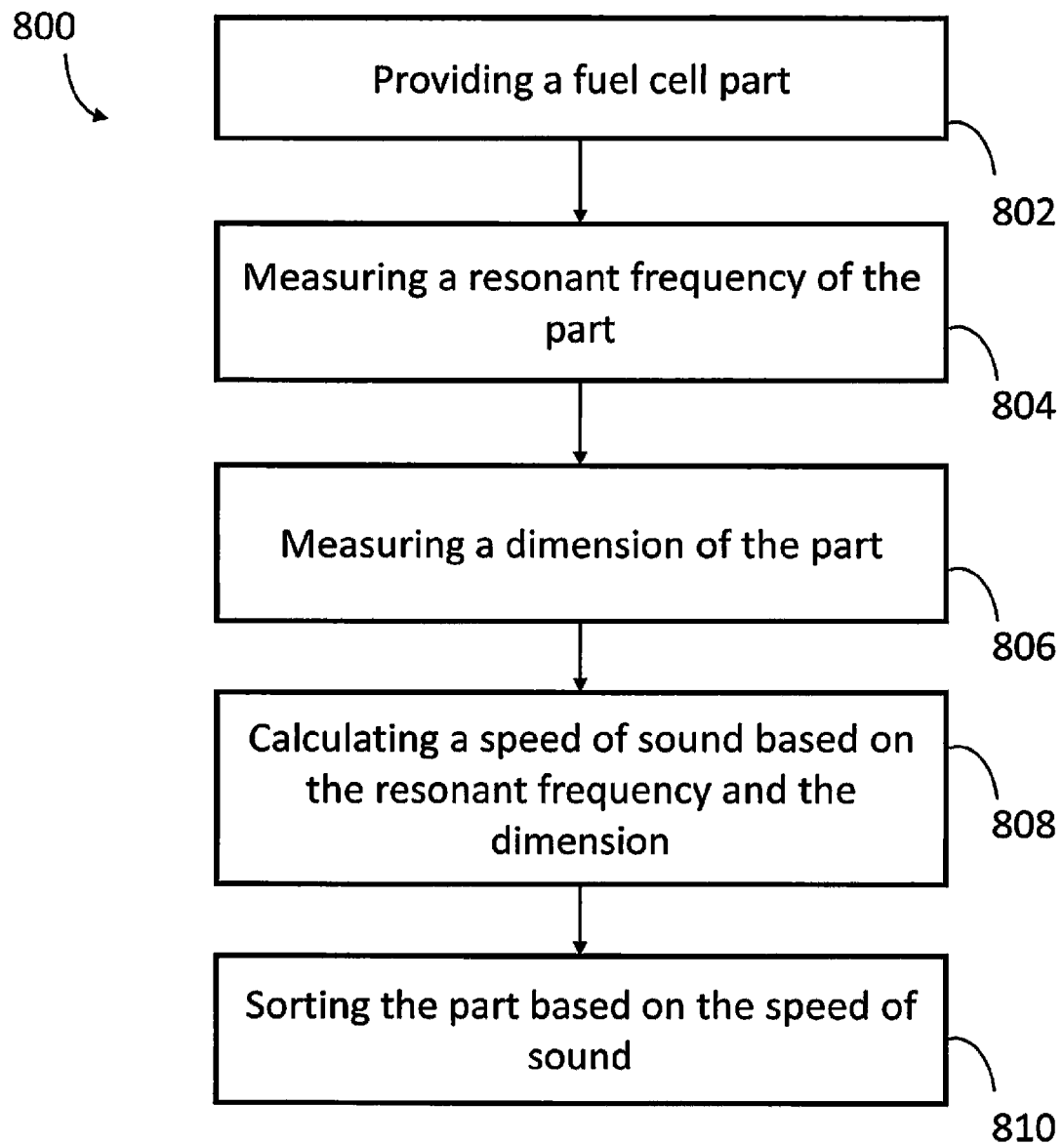
FIG. 8 is a process flow chart illustrating an embodiment method for testing a fuel cell interconnect involving a resonant frequency.

Further embodiments may involve measuring one or more resonant frequencies. FIG. 8 illustrates an embodiment method 800. A fuel cell part may be provided in step 802. A resonant frequency may be measured in step 804. A part may have several resonance frequencies or modes. These modes may be multiples of a lowest frequency or fundamental frequency. Resonant frequency may be measured several different ways. For example, a constant vibration (e.g., acoustic vibration) excitation may be applied to the part. A separate touch probe may be used to read the frequency at which the part resonant. Alternatively, a single ping may be applied, the vibrations may decay as a function of time, and a probe or other transducer may read the resonant frequency. Various embodiments may rely on ultrasound signals for pinging or exciting the fuel cell part.

A dimension of the fuel cell part may be measured in step 806. For example, the dimension X may be measured between the edges of the part. The resonant frequency will have nodes at the edge of the part. Therefore, a speed of sound may be calculated based on the dimension and the resonant frequency in step 808.

The part may be sorted based on the calculated speed of sound in step 810. Sorting may include selecting or deselecting the part for use in a fuel cell stack. Alternatively, various embodiments may omit steps 806, 808, and 810, and the fuel cell part may be sorted based on the resonant frequency. For example, certain ranges of resonant frequencies may be directly correlated with whether to select or deselect the part. The same is also true for the method of FIGS. 7A and 7B where parts may be sorted based on the output of acoustic measurement devices without expressly calculating the speed of sound.

Various embodiments may correlate the resonant frequency or speed of sound in the part with a coefficient of thermal expansion of the part. Further embodiments may rely on a speed of sound or resonant frequency to determine or approximate a coefficient of thermal expansion and sort the fuel cell part based on the coefficient of thermal expansion.

Various embodiments may include measuring the weight of the fuel cell part. The speed of sound may be adjusted based on the weight. For example, the part may be weighed. The volume of the part may be known or calculated based on the measured dimension as well as other measured dimensions. The volume may be used with the weight to calculate the density of the part (e.g. density is a function of weight divided by volume). These measurements may be either average values or a distribution of values across the part. Further embodiments may sort the fuel cell part based on the adjusted speed of sound for weight or based on density.

Figure 9:
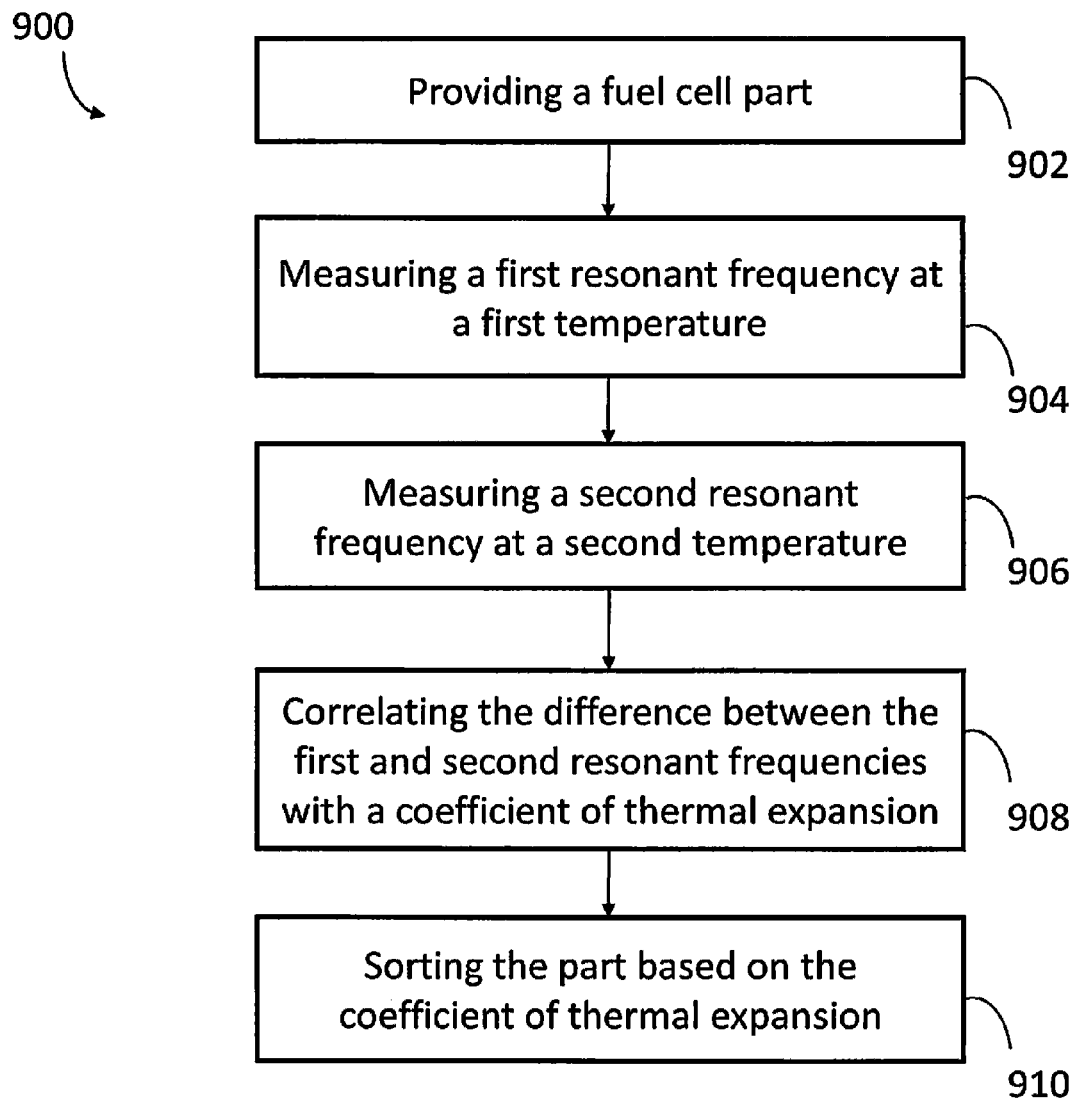
FIG. 9 is a process flow chart illustrating an embodiment method for testing a fuel cell interconnect involving two resonant frequencies.

FIG. 9 illustrates an embodiment method 900 involving multi-temperature measurements of a first and second resonant frequency, but avoiding the need to measure a dimension. A fuel cell part may be provided in step 902. A first resonant frequency may be measured at a first temperature in step 904 (e.g. at room temperature). The resonant frequency may be measured in various ways as discussed above. A second resonant frequency may be measured at a second temperature in step 906 (e.g. above room temperature). The difference between the first and second frequency may be correlated with a coefficient of thermal expansion in step 908. This may be done various ways, such as with a lookup table. A table may be previously generated based on previous fuel cell parts with known values. The complexity of this table may be reduced if certain variables are held constant. For example, the first and second temperatures may be set to predefined values for ease of correlation.

The fuel cell part may be sorted based on the coefficient of thermal expansion in step 910. Sorting may include selecting or deselecting the component to be included in a fuel cell stack. Alternatively, steps 908 and 910 may be omitted and the fuel cell part may be sorted based on the first and second frequencies. For example, certain ranges of resonant frequencies may be directly correlated with whether to select or deselect the part.

Figure 10:
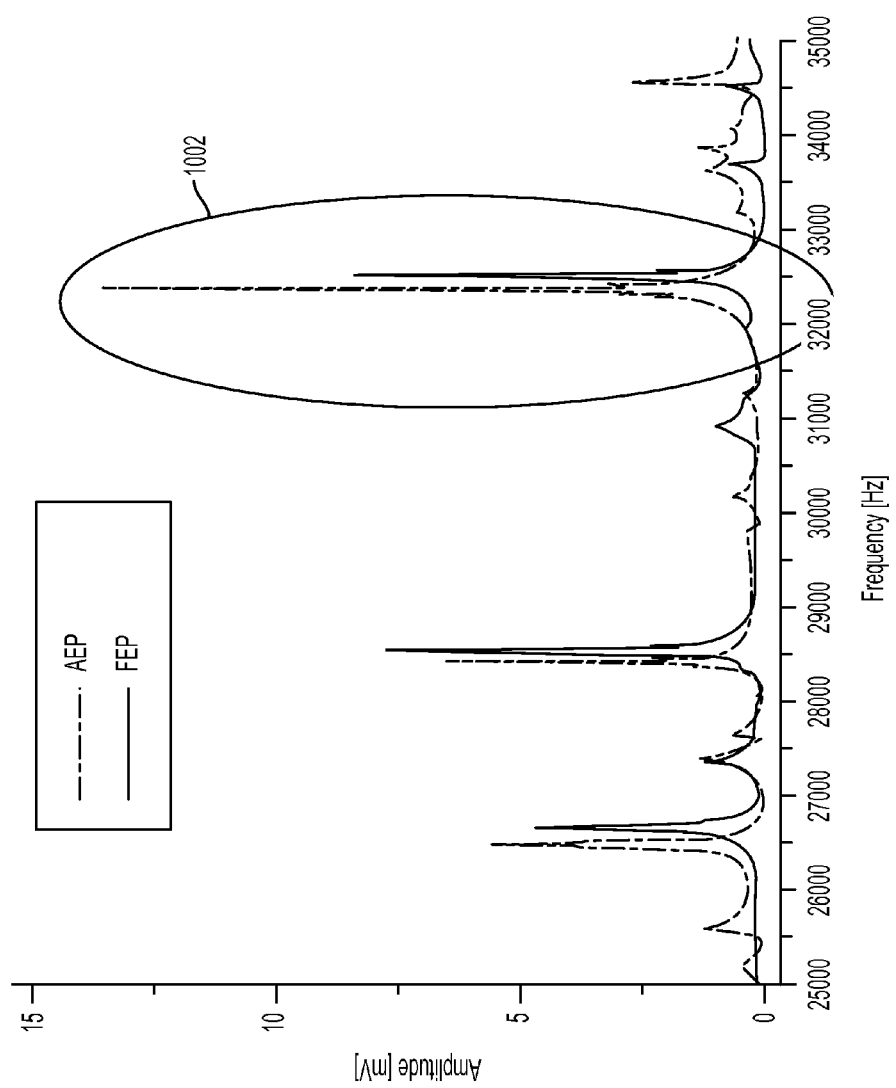
FIG. 10 a plot of frequency scans measured from 25 to 35 KHz on two different fuel cell plates to identify resonance peaks.

FIG. 10 is a plot of experimental data illustrating amplitude across various frequencies of an air end plate or "AEP" (e.g. an end plate adjacent to the cathode of the last cell in a fuel cell stack) and a fuel endplate or "FEP" (e.g. an end plate adjacent to the anode of the opposite last cell in a fuel cell stack). Element 1002 indicates a similar resonance peak of the two end plates. This similar resonance may indicate that the end plates may be used on the same fuel cell stack.

Figure 11:
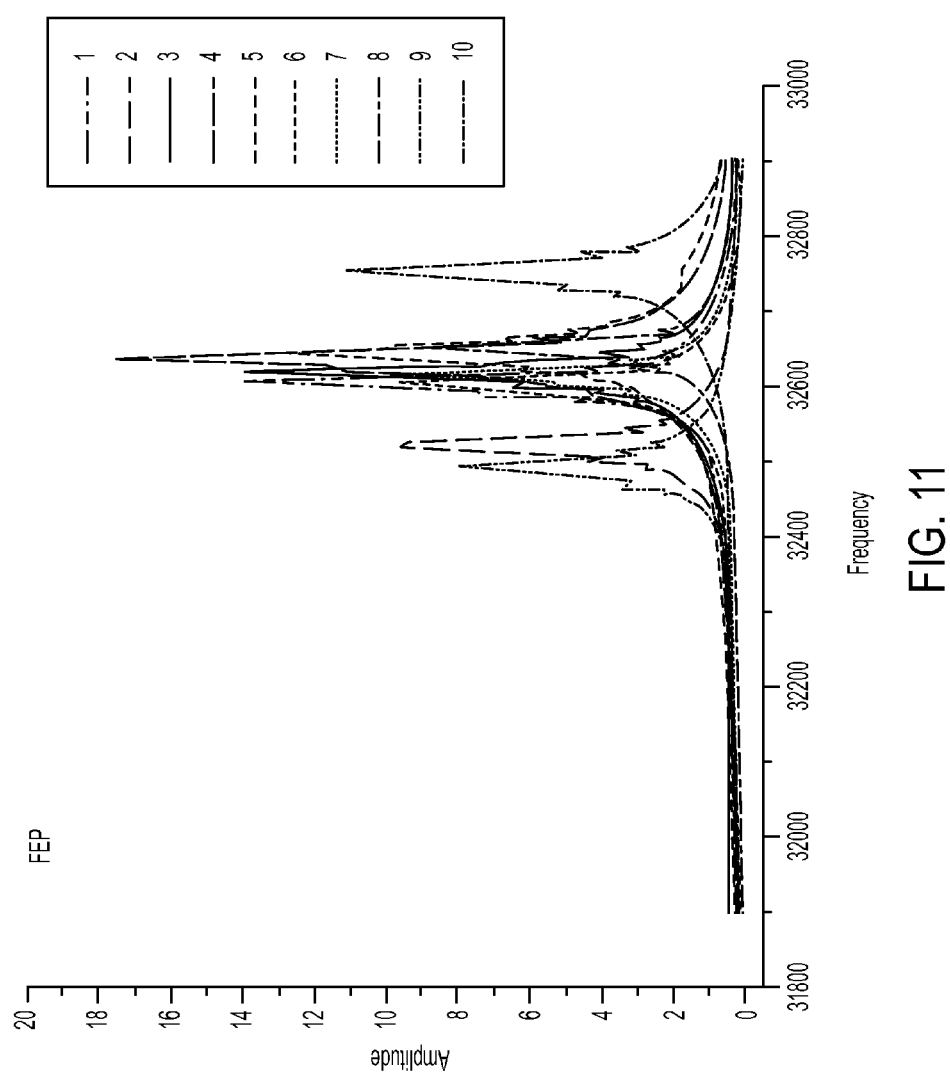
FIG. 11 is a plot of frequency scans measured on multiple fuel end plates in a narrow frequency range.

FIG. 11 illustrates the variation in frequency response between ten different fuel end plates. Similar to the previous graph in FIG. 10, the x axis is frequency and the y axis is amplitude. Despite being from the same batch, the end plates shown in the table of FIG. 11 demonstrate the potential variation in resonance frequency which may indicate differences in density and/or coefficient of thermal expansion amongst the plates.

Figure 12:
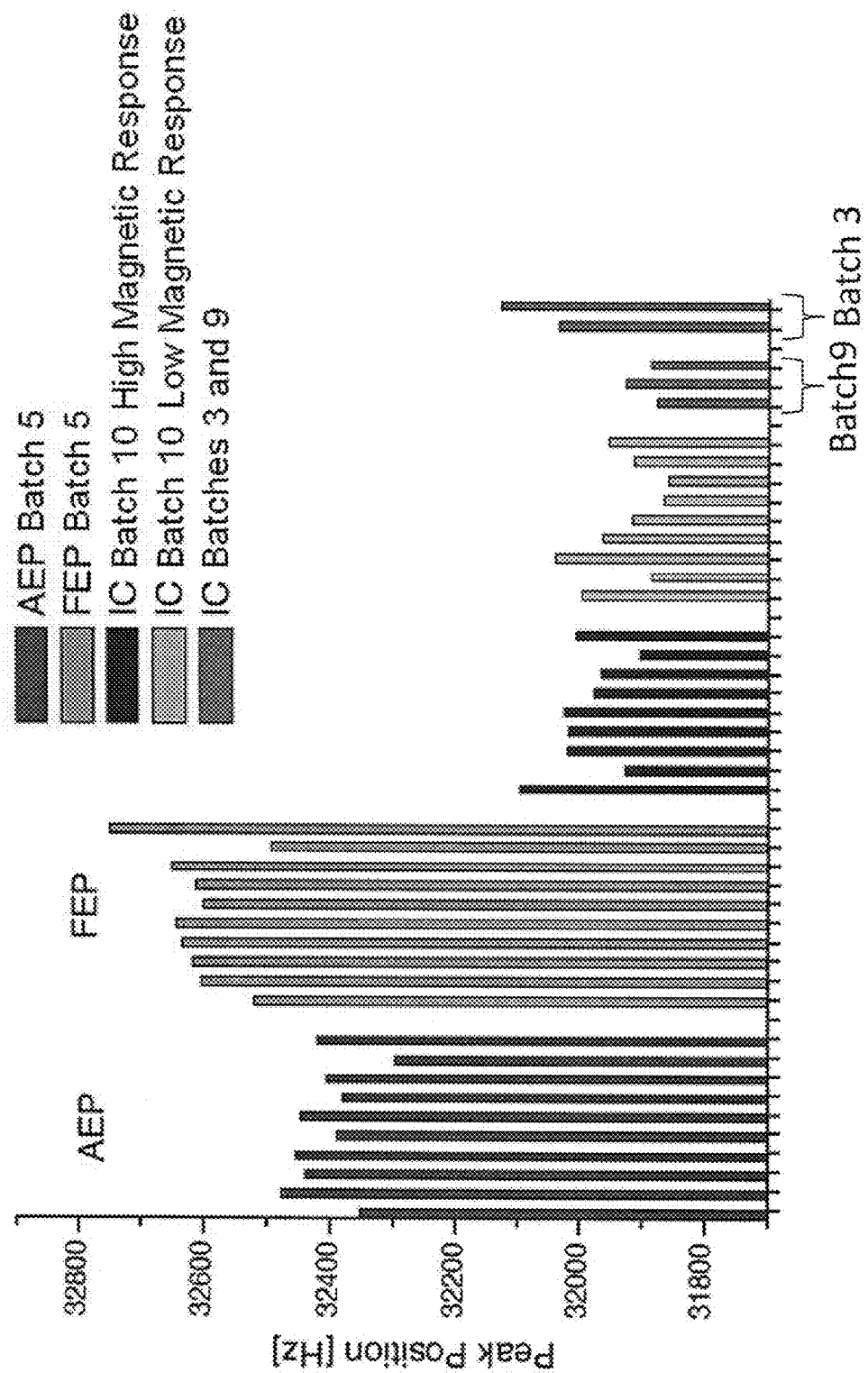
FIG. 12 is a plot of peak resonant frequency positions measured on various fuel cell interconnect plates.

FIG. 12 is a graph of the peak resonance frequency measured for various components. Included are air end plates (AEP), fuel end plates (FEP), and several interconnects (IC, used in the middle of a fuel cell stack) from different production batches. FIG. 12 again illustrates the potential variation between parts (e.g., such as a difference in peak position between IC batches 3 and 9, despite the same IC geometry in both batches). FIG. 12 also illustrates the variation between types of parts. For example, interconnects may generally have a lower resonant frequency. Therefore, the correlations described above may vary based on the fuel cell part involved in the method or even based on production batches. FIG. 12 also includes peak resonance frequencies for interconnects exhibiting different magnetic responses. Interconnects or other fuel cell parts may be sorted according to magnetic response. FIG. 12 illustrates that peak resonant frequency may vary even across interconnects with similar magnetic response such that sorting interconnects by resonant frequency may provide different or improved results compared to sorting by magnetic response.

Corrections for weight and length of the part, as discussed above, may reduce the variation seen in FIGS. 10-12 and improve the various correlations.

Various ultrasound detection and analysis devices may be used in the methods described above. For example, various embodiments may use Resonance Ultrasonic Vibrations (RUV) system from Ultrasonic Technologies Systems of Florida. The RUV system may be a computer controlled mechanical unit providing fast, non-destructive measurements on a production line of parts.

Further embodiments may include non-destructive methods for testing fuel cell parts by active thermography. A fuel cell part, such as an interconnect, may be stimulated by one or more types of energy, such as ultrasound, induction (i.e., inductive heating), or optical energy (e.g., ultraviolet, visible, and/or infrared radiation), and observing the thermal response of the fuel cell part. Defects in the fuel cell part may be detected based on irregularities in the observed thermal response.

Active thermography differs from passive thermography in that an energy source is used to produce a thermal contrast between the test object and its surroundings. For example, an interconnect may be in thermal equilibrium with the background environment. After stimulating the interconnect with energy, the interconnect releases heat to reestablish thermal equilibrium. This release of heat may be observed spatially (i.e., across the interconnect or other part) and temporally (i.e. over time, such as an infrared video or a series of pictures). Various algorithms may be used to determine defects based on this heat imaging. For example, a crack, a void, an impurity, or a delaminated coating (e.g., a perovskite or spinel metal oxide coating on the air side of the interconnect, such as lanthanum strontium manganate or manganese cobalt oxide) in the interconnect may release more heat or at a different rate than a defect free interconnect.

Figure 13:
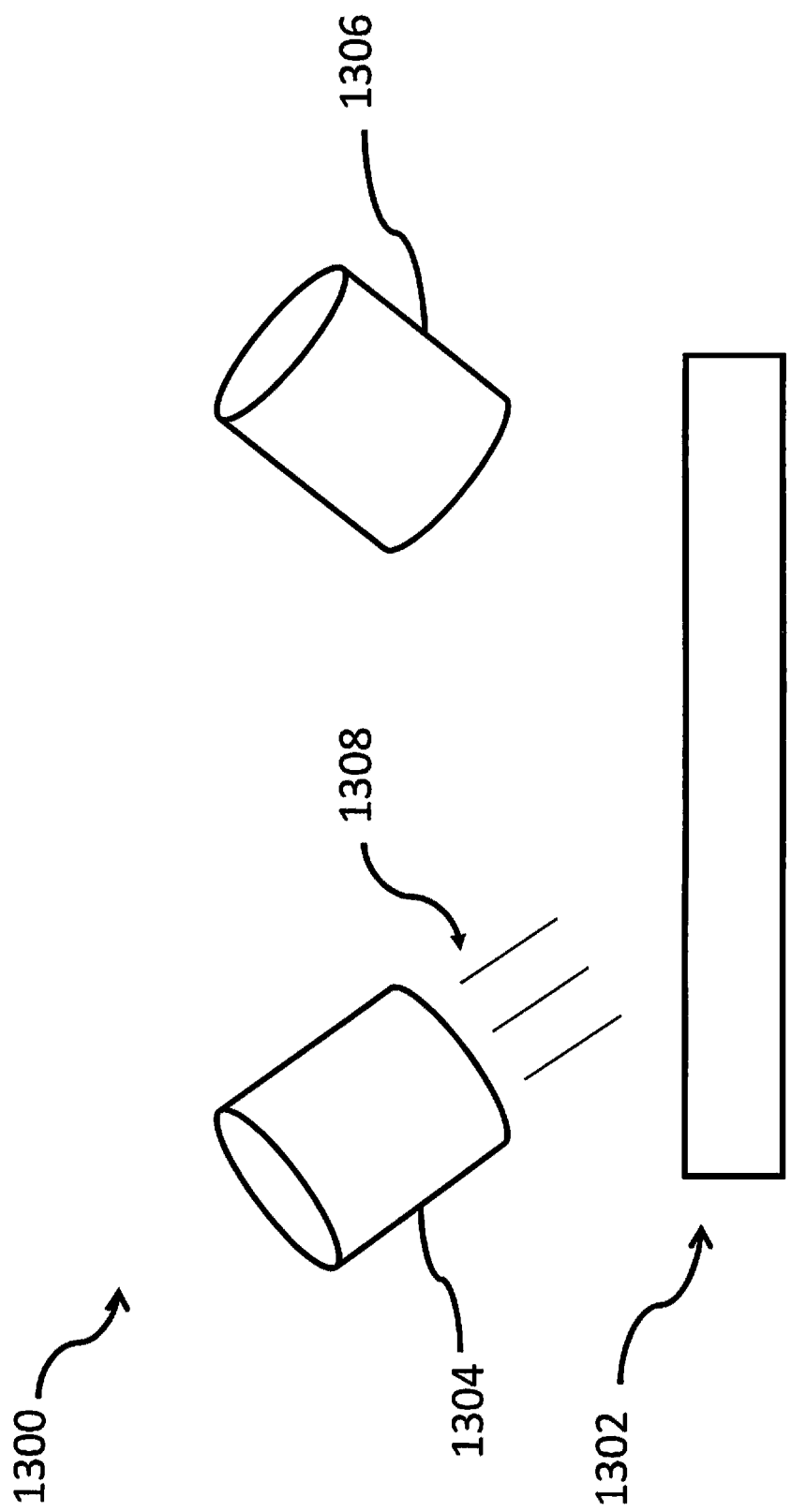
FIG. 13 schematically illustrates a testing apparatus for detecting a defect in a component by measuring a thermal response of the component to optical radiation energy directed at the component.

FIG. 13 illustrates an embodiment system 1300 for using active thermography to test components of a fuel cell. The system 1300 in this embodiment includes at least one source of optical energy 1304 that is configured to direct optical radiation (e.g., ultraviolet, visible, and/or infrared radiation) energy 1308 at a fuel cell component 1302, such as an interconnect. The optical energy source 1304 may be, for example, a flash lamp (e.g., a heating or a photography lamp), halogen lamp, LED, laser source, etc. In one embodiment, the source 1304 can be a high-power, high-frequency photography lamp. The system 1300 also includes at least one detector of thermal energy 1306, which may be an infrared camera or infrared photodetector, for detecting a thermal response of the fuel cell component 1302.

Figure 14:
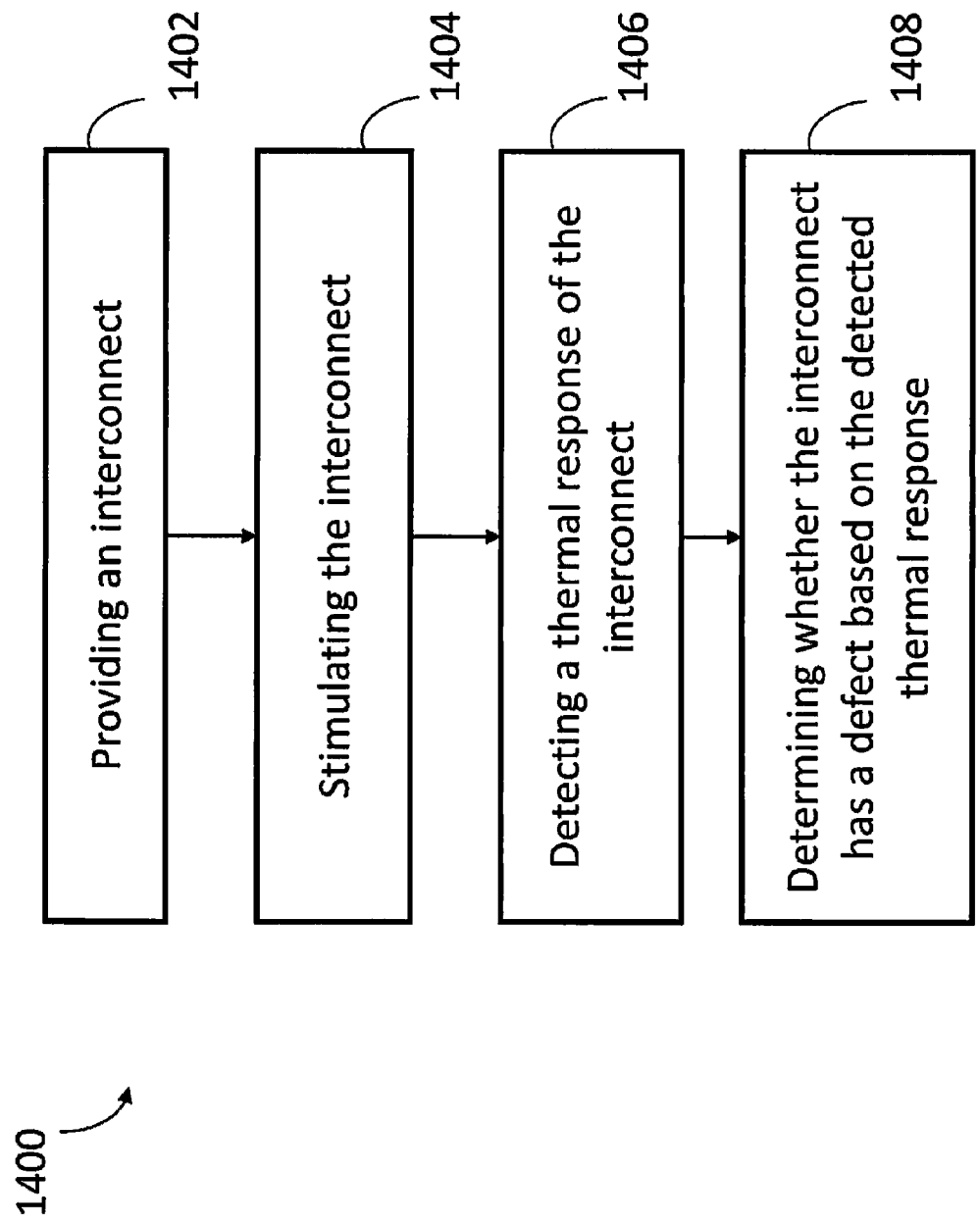
FIG. 14 is a process flow chart illustrating an embodiment method for testing a fuel cell interconnect based on infrared imaging.

FIG. 14 illustrates an embodiment method 1400 for detecting defects in an interconnect. An interconnect may be provided in step 1402. The interconnect may be stimulated in step 1404. Stimulation of the interconnect may be performed various ways. For example, in the embodiment system of FIG. 13, the optical energy source 1304 may stimulate the interconnect with optical energy. Optical energy may be directed at the interconnect in one or more pulses or a prolonged exposure. In various embodiments, the stimulation may be either static or dynamic. For example, a static stimulation may be either a pulse or sustained uniform stimulation having a constant amplitude, peak wavelength, and/or frequency. Dynamic stimulation may vary over time, such as a sweep of frequencies, peak wavelengths, and/or amplitudes (i.e., intensities) of stimulation or various other patterns or sequences. Alternate embodiments may stimulate the interconnect or other part with other energy sources such as ultrasound transducers or inductive coils. These alternate energy source may also provide static or dynamic stimulation.

A thermal response may be detected in step 1406. For example, an infrared camera may record one or more images of the interconnect as it releases thermal energy to reestablish equilibrium with the surroundings. It may be determined whether the interconnect has any defects in step 1408. Defect may be identified from the thermal response. For example, thermal images from an infrared camera could be searched via various algorithms for any irregularities within the image or compared to an image of a defect free interconnect for discrepancies. For example, defects (e.g., cracks, voids, impurities, delaminated metal oxide coating layers (such as lanthanum strontium manganate or manganese cobalt oxide)) may be identified by higher temperature signatures from a spatial thermographic image and/or by lower thermal diffusivities from one or more temporal thermographic images. In another example, thermographic images may be compared to reference thermographic image(s) of acceptable or defect free reference interconnect(s). The interconnects which lack detected defects may be placed into a fuel cell stack, while defective interconnects are not (e.g., they are discarded or sent to be repaired).

Thermal responses or images may be stored or manipulated by a logic device or displayed on a monitor. For example, a thermal energy detector 1306 may be connected to a computer with memory and a processor. The computer or logic device may be programmed with instructions for performing various embodiment methods.

Figure 15:
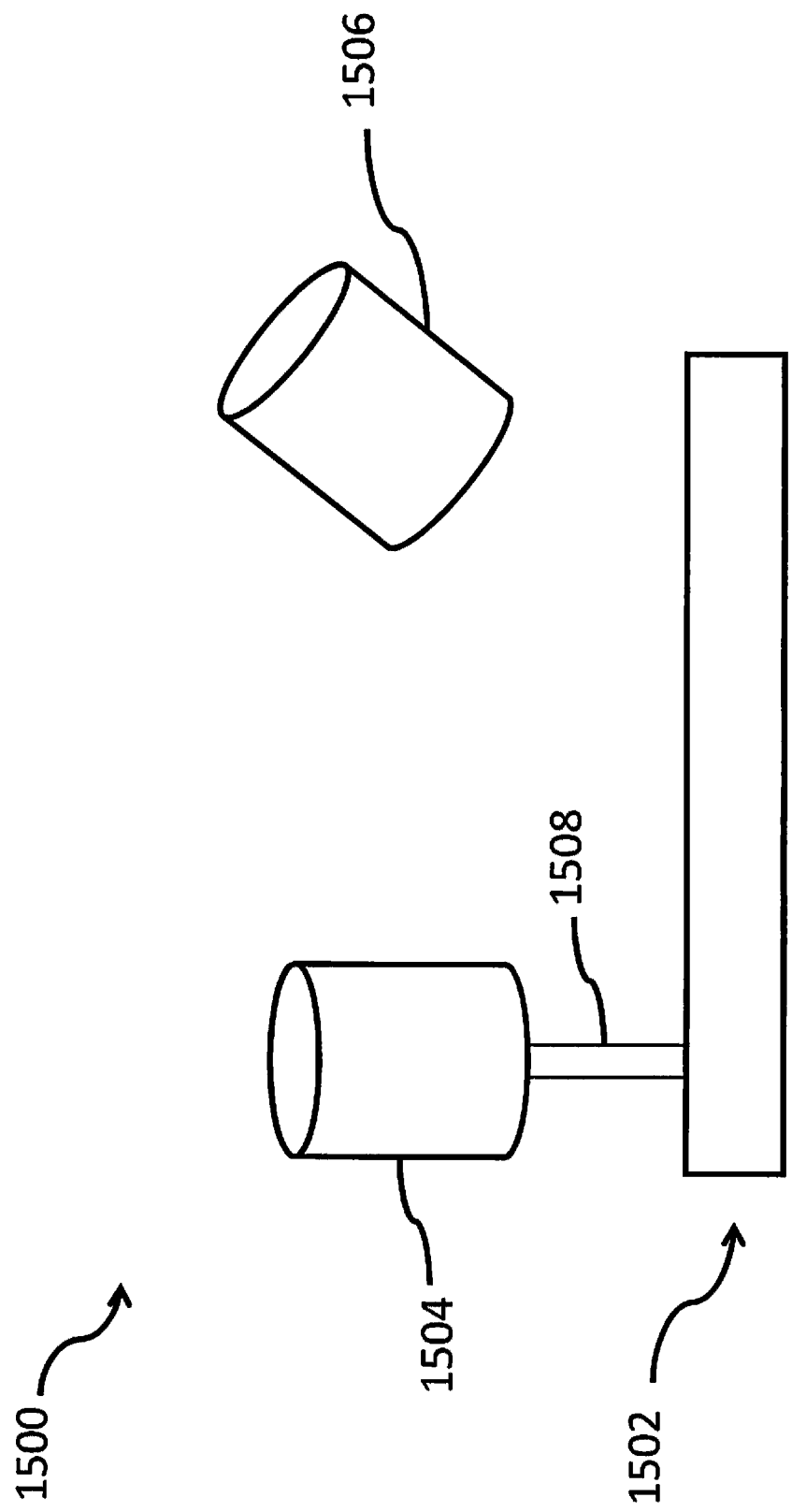
FIG. 15 schematically illustrates a test setup for ultrasonic excitation and infrared imaging.

Further embodiments may include stimulation from an ultrasound transducer. FIG. 15 illustrates an example test setup 1500 for ultrasonic stimulation and infrared imaging of a fuel cell component 1502 (e.g., the interconnect). An interconnect may be stimulated by ultrasound, such as with one or more ultrasound pulses or signals. Ultrasound may be provided by an ultrasound generator 1504 connected to transducer or probe 1508 contacting the interconnect. The system 1500 also includes at least one detector of thermal energy 1506, such as an infrared camera or infrared photodetector, for detecting a thermal response of the fuel cell component 1502.

Figure 16B:
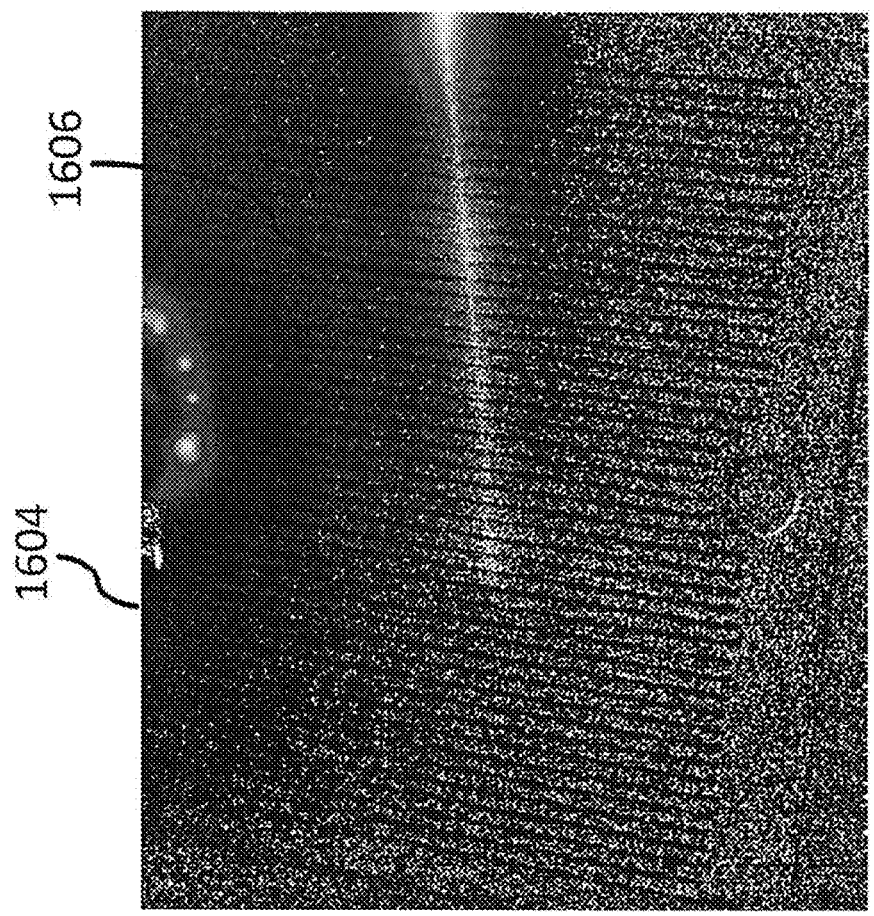
FIGS. 16A and 16B are top views of a sample interconnect with a defect and a schematic of a resulting infrared image, respectively.
Figure 16A:
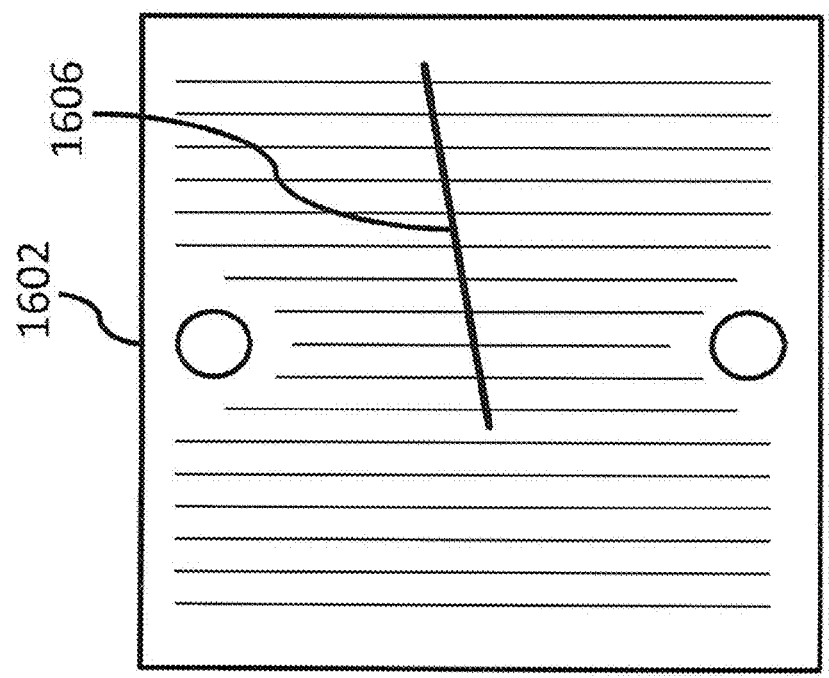

FIGS. 16A and 16B illustrate a sample interconnect with a defect and the resulting infrared image. The interconnect 1602 in FIG. 16A shows a clearly visible line-shaped defect 1606. The infrared image 1604 illustrates how the defect 1606 is visible in a thermal image.

FIGS. 17A and 17B are a series of infrared images showing infrared phase and amplitude, respectively, resulting from sweeping the ultrasonic excitation across the interconnect. FIG. 17A shows images of based on the infrared phase of energy released by an interconnect while FIG. 17B shows images based on the infrared amplitude. The excitation frequency of the images varies from left to right. As shown by the images, generally lower frequencies show larger cracks and defects while higher frequencies show smaller or tighter cracks and defects.

Figure 18:
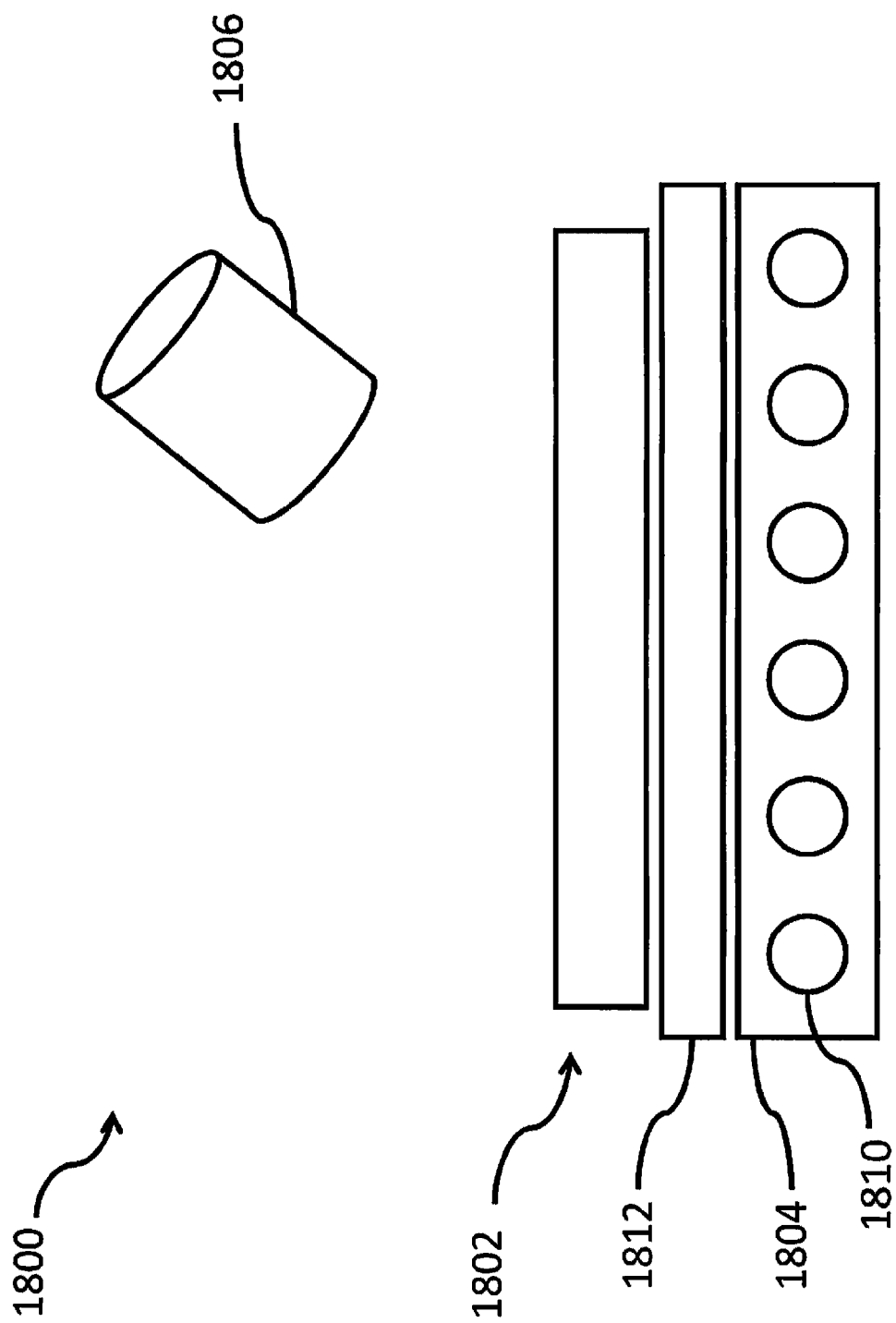
FIG. 18 is schematically illustrates a test setup using a liquid cooled rectangular inductance excitation source and infrared imaging.

Further embodiments may include stimulation from an inductance coil. Inductance coils may vary in shape and power. FIG. 18 illustrates an example test setup 1800 using a liquid cooled manifold 1804 containing rectangular inductance excitation source (i.e., coil) 1810. A cross section of the rectangular inductance coil 1810 is shown in FIG. 18 with the coil coming out of the page such that the rectangular coil appears as circles rather than a rectangle. A stage 1812, such as a wooden (or another material which is not inductively heated) stage not heated by inductive heating, may support the interconnect 1802. An infrared imaging device 1806 may be suspended overhead.

Figures 19A, 19B, 19C:
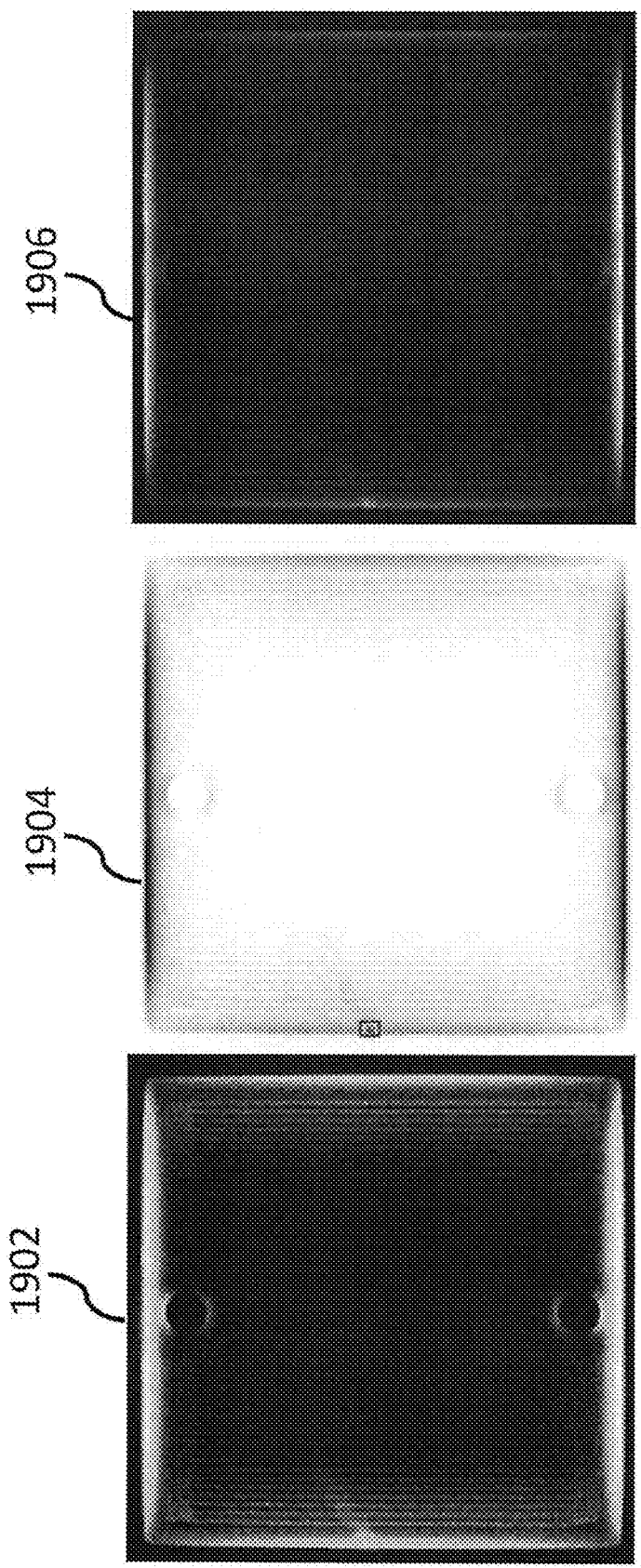
FIGS. 19A-19C are schematic top views of an infrared image of an interconnect, an image in which an area of interest has been identified, and an image where the area is determined to be a defect to be rejected, respectively.

FIGS. 19A-19C are a series of images of an interconnect from an infrared imaging device, such as the one in FIG. 18. Image 1902 in FIG. 19A is an infrared image of an interconnect after being stimulated by an inductance coil. Image 1904 in FIG. 19B shows the same image after an area of interest has been identified, such as by an image analyzing algorithm. Image 1906 in FIG. 19C is the same image again after the area is determined to be a defect to be rejected.

Alternate embodiments may rely on various shapes of inductance coils. Image 2002 in FIG. 20A is an infrared image of an interconnect stimulated by the rectangular inductive coil. Image 2004 in FIG. 20B is an infrared image of an interconnect stimulated by a circular (i.e., spiral with a roughly circular outer diameter) inductive coil. The defect in the interconnect is not visible in the image 2002 when the rectangular inductive coil is used, but when the same interconnect is stimulated with the circular inductive coil, the defect is plainly seen in the middle of the interconnect in image 2004. Therefore, alternate embodiments may rely on inductance coils combining these shapes or other shapes to eliminate blind spots. Further embodiments may include tests with multiple inductance coils.

While solid oxide fuel cell interconnects, end plates, and electrolytes were described above as the tested objects, any other fuel cell interconnects, such as molten carbonate or PEM fuel cell interconnects, or any other metal alloy or compacted metal powder or ceramic objects not associated with fuel cell systems may also be tested using the above methods.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such a wireless signal processing circuit may include circuits for accomplishing the signal measuring and calculating steps described in the various embodiments.

The hardware used to implement the various embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for testing a fuel cell interconnect, comprising:
    providing a fuel cell interconnect;
    performing a non-destructive test on the fuel cell interconnect comprising detecting a magnetic response of the interconnect as a function of position across the interconnect, wherein the magnetic response of the interconnect is detected at a temperature below 50° C.;
    determining a coefficient of thermal expansion as a function of position across the interconnect based on the detected magnetic response; and
    placing the interconnect into a fuel cell stack if at least one of coefficient of thermal expansion uniformity or an average coefficient of thermal expansion is within a predetermined coefficient of thermal expansion condition range.

2. The method of claim 1, wherein placing the interconnect into the fuel cell stack if at least one of coefficient of thermal expansion uniformity and the average coefficient of thermal expansion is within the predetermined coefficient of thermal expansion condition range comprises placing the interconnect into the fuel cell stack if the coefficient of thermal expansion uniformity is within the predetermined coefficient of thermal expansion condition range.

3. The method of claim 1, wherein placing the interconnect into the fuel cell stack if at least one of coefficient of thermal expansion uniformity and the average coefficient of thermal expansion is within the predetermined coefficient of thermal expansion condition range comprises placing the interconnect into the fuel cell stack if the average coefficient of thermal expansion is within the predetermined coefficient of thermal expansion condition range.

4. The method of claim 1, further comprising determining a magnetic susceptibility of the interconnect from detecting the magnetic response of the interconnect and determining the coefficient of thermal expansion of the interconnect based on the determined magnetic susceptibility of the interconnect.

5. The method of claim 4, wherein the magnetic susceptibility is determined as the function of position across the interconnect from detecting the magnetic response of the interconnect.

6. The method of claim 5, wherein the magnetic susceptibility is determined as a function of position across the interconnect by a magnetometer.

7. The method of claim 1, further comprising sorting the interconnect based on a manufacturer or a source of the interconnect.

8. The method of claim 1, wherein the interconnect comprises a Cr—Fe alloy comprising 94 to 96 wt. % Cr and 4 to 6 wt. % Fe.

9. The method of claim 1, wherein placing the interconnect into a fuel cell stack comprises placing the interconnect into a solid oxide fuel cell stack.

10. A method of sorting a fuel cell interconnect, comprising:
    receiving a result of a non-destructive test comprising at least one of a coefficient of thermal expansion of the interconnect or a magnetic susceptibility of the interconnect determined from detecting a magnetic response of the interconnect;
    determining whether the interconnect is within a predetermined coefficient of thermal expansion condition range based on the result, and
    sorting the interconnect based on the determination of whether the interconnect is within the predetermined coefficient of thermal expansion condition range.

11. The method of claim 10, further comprising:
    placing the interconnect into a fuel cell stack when the interconnect is determined to be within the predetermined coefficient of thermal expansion condition range.

12. The method of claim 11, wherein placing the interconnect into a fuel cell stack when the interconnect is determined to be within the predetermined coefficient of thermal expansion condition range comprises placing the interconnect into the fuel cell stack when at least one of a coefficient of thermal expansion uniformity and an average coefficient of thermal expansion is within the predetermined coefficient of thermal expansion condition range.

13. The method of claim 10, wherein the at least one of the coefficient of thermal expansion of the interconnect or the magnetic susceptibility of the interconnect determined from detecting the magnetic response of the interconnect comprises the coefficient of thermal expansion of the interconnect determined from detecting the magnetic response of the interconnect.

14. The method of claim 13, wherein the coefficient of thermal expansion is determined as a function of position across the interconnect from detecting the magnetic response of the interconnect.

15. The method of claim 10, wherein the at least one of the coefficient of thermal expansion of the interconnect or the magnetic susceptibility of the interconnect determined from detecting the magnetic response of the interconnect comprises the magnetic susceptibility of the interconnect determined from detecting the magnetic response of the interconnect.

16. The method of claim 15, wherein the magnetic susceptibility is determined as a function of position across the interconnect from detecting the magnetic response of the interconnect.

17. The method of claim 16, wherein the magnetic susceptibility is determined as the function of position across the interconnect by a magnetometer.

18. The method of claim 15, wherein detecting the magnetic response of the interconnect comprises placing a magnet on a scale such that the magnet is separated by predetermined distance from the interconnect, and measuring a weight reading of the magnet as a function of attraction to the interconnect.

19. The method of claim 10, wherein sorting the interconnect based on the determination of whether the interconnect is within the predetermined coefficient of thermal expansion condition range further comprises sorting the interconnect based on a manufacture or a source of the interconnect.

20. The method of claim 10, wherein the interconnect comprises a Cr—Fe alloy comprising 94 to 96 wt. % Cr and 4 to 6 wt. % Fe.

21. The method of claim 11, wherein placing the interconnect into a fuel cell stack comprises placing the interconnect into a solid oxide fuel cell stack.

\* \* \* \* \*